United States Patent
Combier et al.

(10) Patent No.: US 10,563,214 B2
(45) Date of Patent: *Feb. 18, 2020

(54) USE OF MICROPEPTIDES FOR PROMOTING PLANT GROWTH

(71) Applicants: UNIVERSITE TOULOUSE III-PAUL SABATIER, Toulouse (FR); CENTRE NATIONAL DE LA RECHERCHE SCIENTIFIQUE, Paris (FR)

(72) Inventors: Jean-Philippe Combier, Castanet Tolosan (FR); Dominique Laures-Sergues, Toulouse (FR); Guillaume Becard, Odars (FR)

(73) Assignees: UNIVERSITE TOULOUSE III-PAUL SABATIER, Toulouse (FR); CENTRE NATIONAL DE LA RECHERCHE SCIENTIFIQUE, Paris (FR)

( * ) Notice: Subject to any disclaimer, the term of this patent is extended or adjusted under 35 U.S.C. 154(b) by 41 days.

This patent is subject to a terminal disclaimer.

(21) Appl. No.: 15/314,519

(22) PCT Filed: Jun. 3, 2015

(86) PCT No.: PCT/FR2015/051472
§ 371 (c)(1),
(2) Date: Nov. 29, 2016

(87) PCT Pub. No.: WO2015/185861
PCT Pub. Date: Dec. 10, 2015

(65) Prior Publication Data
US 2017/0211080 A1    Jul. 27, 2017

(30) Foreign Application Priority Data

Jun. 3, 2014  (FR) .................... 14 55045
Jun. 3, 2014  (FR) .................... 14 55046
Mar. 24, 2015  (FR) .................... 15 52469

(51) Int. Cl.
*C07K 14/415*    (2006.01)
*C12N 15/82*    (2006.01)

(52) U.S. Cl.
CPC ........ *C12N 15/8218* (2013.01); *C07K 14/415* (2013.01); *C12N 15/8261* (2013.01)

(58) Field of Classification Search
None
See application file for complete search history.

(56) References Cited

FOREIGN PATENT DOCUMENTS

WO    2015/063431 A1    5/2015

OTHER PUBLICATIONS

Laufs et al. (Development 131.17 (2004): 4311-4322). (Year: 2004).*
GenBank Accession AJ493641, dated Oct. 29, 2007. (Year: 2007).*
Takada et al. (Development 128, 1127-1135 (2001)). (Year: 2001).*
Koyama et al. (The Plant Cell 19.2 (2007): 473-484). (Year: 2007).*
Cui et al. (Current opinion in plant biology 35 (2017): 61-67). (Year: 2017).*
Raman et al. (The Plant Journal 55.1 (2008): 65-76). (Year: 2008).*
French Search Report, dated Jan. 23, 2015, from corresponding French application.
Hui-Shan Guo et al., "MicroRNA Directs mRNA Cleavage of the Transcription Factor NAC1 to Downregulate Auxin Signals for Arabidopsis Lateral Root Development", The Plant Cell, May 2005, pp. 1376-1386, vol. 17, No. 5.
Patrick Laufs et al., "MicroRNA regulation of the CUC genes is required for boundary size control in Arabidopsis meristems", Development, Sep. 2004, pp. 4311-4322, vol. 131, No. 17.
Krisztina Nikovics et al., "The Balance between the MIR164A and CUC2 Genes Controls Leaf Margin Serration in Arabidopsis", The Plant Cell, Nov. 2006, pp. 2929-2945, vol. 18, No. 11.
Florian Bardou et al., "Dual RNAs in plants", Biochimie, Nov. 2011, pp. 1950-1954, vol. 93, No. 11.
Jeroen Crappe et al., "Little things make big things happen: A summary of micropeptide encoding genes", ScienceDirect, EUPA Open Proteomics, 2014, pp. 128-137, vol. 3.
Barbara De Coninck et al., "Mining the genome of Arabidopsis thaliana as a basis for the identification of novel bioactive peptides involved in oxidative stress tolerance", Journal of Experimental Botany, Dec. 2013, pp. 5297-5307, vol. 64, No. 17.
Gong-Ke Zhou et al., "Overexpression of miR165 Affects Apical Meristem Formation, Organ Polarity Establishment and Vascular Development in Arabidopsis", Plant Cell Physiology, Mar. 2007, pp. 391-404, vol. 48, No. 3.
Dominique Lauressergues et al., "Primary transcripts of microRNAs encode regulatory peptides", Nature, Apr. 2015, pp. 90-104, vol. 520, No. 7545.
Kiaozhen Yao et al., "Two types of cis-acting elements control the abaxial epidermis-specific transcription of ht eMIR165a and MIR166a genes", FEBS Letters, Nov. 2009, pp. 3711-3717, vol. 583, No. 22.
International Search Report, dated Nov. 13, 2015, from corresponding PCT application.
Yanfei Mao et al.: "microRNA319a-Targeted *Brassica rapa* ssp. pekinensis TCP Genes Modulate Head Shape in Chinese Cabbage by Differential Cell Division Arrest in Leaf Regions", Plant Physiology, Dec. 18, 2013, pp. 710-720, vol. 164, No. 2.
Chunhua Yang et al.: "Overexpression of microRNA319 impacts leaf morphogenesis and leads to enhanced cold _olerance in rice (*Oryza sativa* L.) ", Plant, Cell & Environment, May 30, 2013, pp. 2207-2218, vol. 36, No. 12.
Man Zhou et al.: "Constitutive Expression of a miR319 Gene Alters Plant Development and Enhances Salt and Drought Tolerance in Transgenic Creeping Bentgrass", Plant Physiology, Jan. 4, 2013, pp. 1375-1391, vol. 161, No. 3.

* cited by examiner

*Primary Examiner* — Charles Logsdon
(74) *Attorney, Agent, or Firm* — Maier & Maier, PLLC

(57) ABSTRACT

The present invention relates to the use of micropeptides (peptides encoded by microRNAs or "miPEPs") for promoting plant growth.

Figure 1:
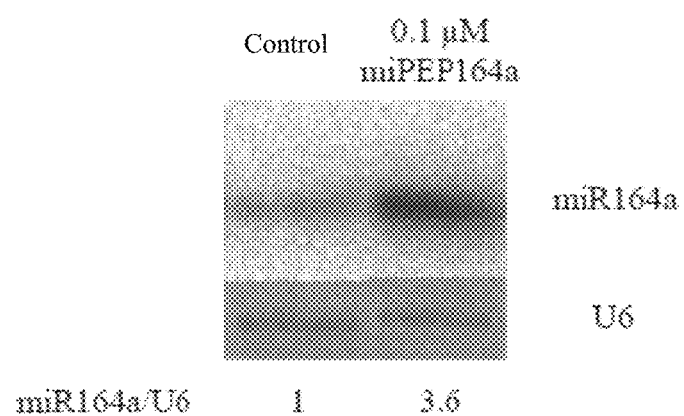

6 Claims, 6 Drawing Sheets
Specification includes a Sequence Listing.

A) Control plant

B) Plant treated with miPEP 164a

A) Control plant

B) Plant treated with miPEP319a

SEQUENCE LISTING

<160> NUMBER OF SEQ ID NOS: 12

<210> SEQ ID NO 1
<211> LENGTH: 21
<212> TYPE: RNA
<213> ORGANISM: Arabidopsis thaliana

<400> SEQUENCE: 1
uggagaagca gggcacgugc a                                            21

<210> SEQ ID NO 2
<211> LENGTH: 37
<212> TYPE: PRT
<213> ORGANISM: Arabidopsis thaliana

<400> SEQUENCE: 2

Met Pro Ser Trp His Gly Met Val Leu Leu Pro Tyr Val Lys His Thr
1               5                   10                  15

His Ala Ser Thr His Thr His Thr His Asn Ile Tyr Gly Cys Ala Cys
            20                  25                  30

Glu Leu Val Phe His
        35

<210> SEQ ID NO 3
<211> LENGTH: 114
<212> TYPE: DNA
<213> ORGANISM: Arabidopsis thaliana

<400> SEQUENCE: 3

```
atgccatcat ggcatggtat ggttctttttg ccttacgtaa aacacactca cgccagcaca      60
cacacacaca cacataacat atacggatgt gcgtgtgagc tagtcttcca ttaa            114
```

<210> SEQ ID NO 4
<211> LENGTH: 466
<212> TYPE: DNA
<213> ORGANISM: Arabidopsis thaliana

<400> SEQUENCE: 4

```
agacaagccc ccacactaaa aaacagtaa tatggaataa aaaaaagctt tcaaaactta       60
gcagttatta gacaaggtat tgtttggccc tagctagcga tcgtttagct ctcttcactc     120
tctcactttt ttagttcaac ccttcttttg cgtgagatgc catcatggca tggtatggtt     180
cttttgcctt acgtaaaaca cactcacgcc agcacacaca cacacacaca taacatatac     240
ggatgtgcgt gtgagctagt cttccattaa tgcaatcttt gggcctatat atacaaacct     300
ttccataacc aaagttctca tactacaaac gcccctcatg tgcttggaaa tgcgggtgag     360
aatctccatg ttggagaagc agggcacgtg caaaccaaca aacacgaaat ccgtctcatt     420
tgcttatttg cacgtactta acttctccaa catgagctct tcaccc                    466
```

<210> SEQ ID NO 5
<211> LENGTH: 21
<212> TYPE: RNA
<213> ORGANISM: Arabidopsis thaliana

<400> SEQUENCE: 5

```
ucggaccagg cuucauccccc c                                                21
```

<210> SEQ ID NO 6
<211> LENGTH: 18
<212> TYPE: PRT
<213> ORGANISM: Arabidopsis thaliana

<400> SEQUENCE: 6

```
Met Arg Val Lys Leu Phe Gln Leu Arg Gly Met Leu Ser Gly Ser Arg
1               5                   10                  15

Ile Leu
```

<210> SEQ ID NO 7
<211> LENGTH: 57
<212> TYPE: DNA
<213> ORGANISM: Arabidopsis thaliana

<400> SEQUENCE: 7

```
atgagggtta agctatttca gttgagggga atgttgtctg gatcgaggat attatag         57
```

<210> SEQ ID NO 8
<211> LENGTH: 484
<212> TYPE: DNA
<213> ORGANISM: Arabidopsis thaliana

<400> SEQUENCE: 8

```
ctagggttta ggaatgacga cctgtttctg ttgtgtctta ttaaaagccc atcttcgtct      60
```

```
ccgccactca tcattccctc atcataacac catcatcacc attcaccaac ctctctctct      120
ctctcctcta tcactctcta caacaaaaat ttgtgaatct gctaagatcg attatcatga      180
gggttaagct atttcagttg aggggaatgt tgtctggatc gaggatatta tagatatata      240
catgtgtatg ttaatgattc aagtgatcat agagagtatc ctcggaccag gcttcatccc      300
ccccaacatg ttattgcctc tgatcaccat ttattgttac attttttttt gttaattact      360
tgcgcaaatt acaaaagctt ggttttgtg atgactttga atctttcttg catggcttct       420
taagagtaga tttacggatc cgtctatgct ttttgctttt tgtttcgttt atttgtattt      480
aaac                                                                  484

<210> SEQ ID NO 9
<211> LENGTH: 21
<212> TYPE: RNA
<213> ORGANISM: Arabidopsis thaliana

<400> SEQUENCE: 9
uuggacugaa gggagcuccc u                                                21

<210> SEQ ID NO 10
<211> LENGTH: 50
<212> TYPE: PRT
<213> ORGANISM: Arabidopsis thaliana

<400> SEQUENCE: 10

Met Asn Ile His Thr Tyr His His Leu Leu Phe Pro Ser Leu Val Phe
1               5                   10                  15

His Gln Ser Ser Asp Val Pro Asn Ala Leu Ser Leu His Ile His Thr
            20                  25                  30

Tyr Glu Tyr Ile Ile Val Val Ile Asp Pro Phe Arg Ile Thr Leu Ala
        35                  40                  45

Phe Arg
    50

<210> SEQ ID NO 11
<211> LENGTH: 153
<212> TYPE: DNA
<213> ORGANISM: Arabidopsis thaliana

<400> SEQUENCE: 11
atgaatatac atacatacca tcatcttctt ttcccatctc tagttttcca tcaatcttct       60
gatgttccaa acgctctatc tcttcatata catacatacg aatatattat tgttgtcata      120
gatccattta gaatcacttt agcttttaga tga                                   153

<210> SEQ ID NO 12
<211> LENGTH: 646
<212> TYPE: DNA
<213> ORGANISM: Arabidopsis thaliana

<400> SEQUENCE: 12
ttgtatccgc agtgtatttc ctcgcatcta ccatcccttt tctacgcctc tctccctctc       60
tctctttctc catcaaatct tgttttgttc aaactctctc tctctcatct attctctcca      120
tacaatacat gaatatacat ataccatc atcttctttt cccatctcta gtttttcatc       180
aatcttctga tgttccaaac gctctatctc ttcatataca tacatacgaa tatattattg      240
ttgtcataga tccatttaga atcacttag cttttagatg agatctaggg tttcttgtt       300 ttctttcaaa ttttgttgca tattcttcta aatcatggtt tttcgcttgc taggttatag      360
```

```
atccatgcaa atatggagta gatgtacaaa cacacgctcg gacgcatatt acacatgttc    420
atacacttaa tactcgctgt tttgaattga tgttttagga atatatatgt agagagagct    480
tccttgagtc cattcacagg tcgtgatatg attcaattag cttccgactc attcatccaa    540
ataccgagtc gccaaaattc aaactagact cgttaaatga atgaatgatg cggtagacaa    600
attggatcat tgattctctt tgattggact gaagggagct ccctct                  646
```

USE OF MICROPEPTIDES FOR PROMOTING PLANT GROWTH

The present invention relates to the use of micropeptides (peptides encoded by microRNAs or "miPEPs") for promoting plant growth.

MicroRNAs (miRNAs) are small non-encoding RNAs, of about 21 nucleotides after maturation, which control the expression of target genes at the post-transcriptional level, by degrading the target mRNA or inhibiting translation thereof.

In particular, miRNAs are encountered in plants. The genes targeted by the miRNAs are often key genes in developmental processes. For example, the miR164s target genes of the CUC family (Blein et al., *Science*, 322(5909): 1835-9, 2008). The miR164 family is thus involved in the development of meristems and in particular in leaf development (Laufs et al., *Development*, 131(17):4311-22, 2004; Nikovics et al., *Plant Cell*, 18(11):2929-45, 2006). In another example, miR319s target transcription factors of the TCP family, involved in cell growth (Nag et al., *Proc Natl Acad Sci USA*, 106(52):22534-9, 2009). Overexpression of miR319a thus leads to a foliar phenotype (Jaw phenotype, Palatnik et al., *Nature*, 425(6955):257-63, 2003) as well as a floral phenotype (Nag et al., 2009).

Therefore, through their action of regulating the expression of certain genes, the miRNAs could represent a target of interest for controlling plant growth, and in particular for promoting plant growth.

Very little is known about regulation of the expression of miRNAs, but it has been demonstrated that the latter involves, like most encoding genes, an RNA polymerase II: this enzyme produces a primary transcript, called "pri-miRNA", which is then matured by a protein complex containing in particular enzymes of the Dicer type. This maturation leads firstly to formation of a miRNA precursor called "pre-miRNA", having a secondary structure of stem-loop form containing the miRNA and its complementary sequence miRNA*. Then the precursor is matured, which leads to formation of a shorter double-stranded RNA containing the miRNA and the miRNA*. The miRNA then comes under the control of the RISC complex, which cleaves the mRNA of the target gene or inhibits its translation.

To date, the miRNAs, and by extension their primary transcript, have always been regarded, on account of their particular mode of action, as non-encoding regulatory RNAs that do not produce any peptide. Now, the inventors have recently demonstrated, in patent application FR 13/60727, the existence of micropeptides (or "miPEPs", microRNA encoded PEPtides) capable of modulating the accumulation of miRNAs.

In this context, the purpose of the present invention is to propose novel, effective and environmentally friendly tools for promoting plant growth.

One aspect of the invention is to propose a novel use of miPEPs for promoting plant growth.

Another aspect of the invention also relates to a novel method for cultivating plants.

Another aspect of the invention is to propose a composition of miPEPs making it possible to promote plant growth.

Another aspect of the invention is also to propose a transgenic plant and parts of transgenic plants, and the production method thereof.

Another aspect of the invention is also to propose organs, cells and seeds of transgenic plants.

Another aspect of the invention is to propose environmentally friendly modified plants.

The invention therefore relates to the use of a peptide for promoting plant growth, said peptide being introduced into the plant, said peptide having an amino acid sequence comprising or consisting of a sequence identical to that of a miPEP naturally present in said plant, said miPEP naturally present in said plant being a peptide of 3 to 100 amino acids, in particular 4 to 100 amino acids, the sequence of which is encoded by an open reading frame situated on the primary transcript of a miRNA, said miPEP being capable of modulating the accumulation of said miRNA in said plant, said miRNA regulating the expression of at least one gene involved in the development of the vegetative or reproductive parts of the plant, in particular the roots, the stem, the leaves or the flowers.

Surprisingly and unexpectedly, the inventors found that the use of peptides the sequence of which comprises or consists of a sequence identical to that of miPEPs encoded on the primary transcripts of miRNAs makes it possible to promote plant growth.

In the invention, the terms "microRNA", "non-encoding microRNA" and "miRNA" are equivalent and may be used interchangeably. They define small RNA molecules of about 21 nucleotides, which are not translated and do not lead to a peptide or a protein. However, in this mature form, the miRNAs perform a function of regulation of certain genes by post-transcriptional mechanisms, for example via the RISC complex.

The "primary transcript of miRNA" (or "pri-miRNA") for its part corresponds to the RNA molecule directly obtained from transcription of the DNA molecule. Generally, this primary transcript undergoes one or more post-transcriptional modifications, which lead for example to a particular structure of the RNA or a cleavage of certain parts of the RNA by splicing phenomena, and which lead to the precursor form of the miRNA (or "pre-miRNA"), and then to the mature form of the miRNA.

The terms "micropeptides" and "miPEPs" (microRNA encoded PEPtides) are equivalent and may be used interchangeably. They define a peptide that is encoded by an open reading frame present on the primary transcript of a miRNA, and that is capable of modulating the accumulation of said miRNA. The miPEPs in the sense of the present invention must not be understood as necessarily being peptides of small size, as "micro" does not refer to the size of the peptide.

As stated in patent application FR 13/60727, the contents of which are to be regarded as forming part of the present application, the miPEPs are peptides:
  from 4 to 100 amino acids, preferably from 4 to 60 amino acids, in particular of 4 to 59 amino acids,
  encoded by an open reading frame contained in the primary transcript of a miRNA, preferably in the 5' part of the primary transcript of said miRNA, and
  capable of modulating the accumulation of said miRNA in a eukaryotic cell.

The terms "open reading frame" or "ORF" are equivalent and may be used interchangeably. They correspond to a nucleotide sequence in a DNA or RNA molecule that may potentially code for a peptide or a protein: said open reading frame begins with a start codon (the start codon generally encoding for a methionine), followed by a series of codons (each codon encoding for an amino acid), and ends with a stop codon (the stop codon not being translated).

In the invention, the ORFs may be called specifically "miORFs" when the latter are present on the primary transcripts of miRNA.

The miORFs as defined in the invention may have a size from 15 to 303 nucleotides. As an amino acid is encoded by a codon of 3 nucleotides, the miORFs from 15 to 303 nucleotides code for miPEPS from 4 to 100 amino acids.

In particular, the miORFs have a size of:

15, 18, 21, 24, 27, 30, 33, 36, 39, 42, 45, 47, 51, 54, 57, 60, 63, 66, 69, 72, 75, 78, 81, 84, 87, 90, 93, 96, 99, 102, 105, 108, 111, 114, 117, 120, 123, 126, 129, 132, 135, 138, 141, 144, 147, 150, 153, 156, 159, 162, 165, 168, 171, 174, 177, 180, 183, 186, 189, 192, 195, 198, 201, 204, 207, 210, 213, 216, 219, 222, 225, 228, 231, 234, 237, 240, 243, 246, 249, 252, 255, 258, 261, 264, 267, 270, 273, 276, 279, 282, 285, 288, 291, 294, 297, 300 or 303 nucleotides, and code respectively for miPEPs having a size of:

4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100 amino acids.

A miPEP may also have a size of 3 amino acids.

Taking into account the degeneration of the genetic code, one and the same miPEP may be encoded by several nucleotide sequences. Such nucleotide sequences, differing from one another by at least one nucleotide but encoding for one and the same peptide, are called "degenerated sequences".

In the invention, the term "plant" refers generally to all or part of a plant whatever its stage of development (including the plant in the form of a seed or a young shoot), to one or more organs of the plant (for example the leaves, roots, stem, flowers), to one or more cells of the plant, or to a cluster of cells of the plant.

In the invention, the term "growth" refers to the development of all or part of a plant over time. The growth of the plant may thus be determined and quantified by monitoring evolving parameters observable for certain parts, cells or organs of the plant, such as the leaves, the roots, the stems or the flowers.

Non limitatively, the parameters for determining and quantifying the growth of a plant may in particular be:
  the size, surface area, volume, weight and number of leaves,
  the shape of the leaves,
  the size and number of flowers,
  the size of the stem (or of the floral stalk),
  the root biomass
  the number, length and degree of branching of the roots,
  precocity of germination,
  germinative vigour and duration of the juvenile phase,
  precocity of budding,
  precocity of induction of flowering (or floral transition),
  or also the number of cells.

Moreover, in the invention, the expression "promote plant growth", or "improve plant growth", indicates:
  either an acceleration of development (for example a larger leaf size for a plant at a given point in time relative to a reference plant),
  or an increase in development (for example a larger leaf size for a plant, which cannot be attained by a reference plant),
  or an acceleration and an increase in the development of the plant.

It is important to note that the use according to the invention has the advantage of being environmentally friendly, compared to the chemical methods used conventionally in applied botany or in agriculture, as the miPEP is a peptide that is present naturally in the plant.

The invention also relates to the use of a miPEP introduced exogenously into a plant for promoting its growth,
  said miPEP introduced exogenously being a peptide comprising, or consisting of, a sequence identical to that of a miPEP naturally present in said plant,
  said miPEP naturally present is a peptide of 3 to 100 amino acids, in particular of 4 to 100 amino acids, the sequence of which is encoded by an open reading frame situated at 5' on the primary transcript of a miRNA,
  said miPEP being capable of modulating the accumulation of said miRNA in said plant, and said miRNA regulates the expression of at least one gene involved in the development of the vegetative or reproductive parts of the plant, in particular the roots, the stem, the leaves or the flowers,
  the sum of the quantity of said miPEP introduced exogenously and that of said miPEP that is present naturally being strictly greater than the quantity of said miPEP that is present naturally.

In the invention, the expression "miPEP introduced exogenously" refers to a miPEP introduced into the plant artificially, whether or not the latter is naturally present in the plant.

If the miPEP occurs naturally in the plant, it is an "miPEP of endogenous origin".

If the miPEP does not occur naturally in the plant, it is an "miPEP of exogenous origin". When an "miPEP of exogenous origin" is introduced into the plant, it is then also necessary to introduce the corresponding miRNA and its primary transcript.

Introduction of a miPEP exogenously into the plant therefore involves a technical step; said step is not a natural phenomenon and does not correspond to crossing or to selection.

The miPEP introduced exogenously may either be a peptide produced outside of the plant (for example an isolated and/or purified peptide, a synthetic peptide or a recombinant peptide), or a peptide produced in the plant following the non-natural introduction of a nucleic acid encoding for said miPEP in said plant.

The plant in which the miPEP has not been introduced has a basal quantity of said miPEP, which corresponds to that of said miPEP that is present naturally. The use of a miPEP comprising, or consisting of, a sequence identical to that of said miPEP leads to an increase in the total quantity of miPEP, which modulates the accumulation of the miRNA the primary transcript of which contains the sequence encoding for said miPEP.

Moreover, the miPEP introduced is present in the plant and its introduction does not affect its stability.

In the invention, by "accumulation" is meant the production of a molecule, such as a miRNA or a miPEP, in the cell.

Thus, "modulation of the accumulation" of a molecule in a cell corresponds to a change in the quantity of this molecule in the cell.

In an embodiment, the invention relates to the use as defined above, in which the modulation of the accumulation of said miRNA is a decrease or an increase in the accumulation of said miRNA, in particular an increase.

A "decrease in the accumulation of miRNA" corresponds to a lowering of the quantity of said molecule in the cell.

Conversely, an "increase in the accumulation of miRNA" corresponds to an increase in the quantity of said molecule in the cell.

In an embodiment, the invention relates to the use as defined above, in which said gene that is involved in the development of the vegetative or reproductive parts of the plant is selected from the group consisting of: NAC1 (Accession No. AT1G56010.1), NAC4 (Accession No. AT5G07680.1), NAC5 (Accession No. AT5G61430.1), CUC1 (Accession No. AT3G15170.1) and CUC2 (Accession No. AT5G53950.1) (accession numbers according to the database The *Arabidopsis* Information Resource "TAIR").

In an embodiment, the invention relates to the use as defined above, in which said miRNA is miR164a, in particular in which said miR164a has a nucleotide sequence consisting of SEQ ID NO: 1.

In an embodiment, the invention relates to the use as defined above, in which said miRNA is miR164a, in particular in which said miR164a has a nucleotide sequence consisting of SEQ ID NO: 1, and said gene that is involved in the development of the vegetative or reproductive parts of the plant is selected from the group consisting of: NAC1 (Accession No. AT1G56010.1), NAC4 (Accession No. AT5G07680.1), NAC5 (Accession No. AT5G61430.1), CUC1 (Accession No. AT3G15170.1) and CUC2 (Accession No. AT5G53950.1) (accession numbers according to the database The *Arabidopsis* Information Resource "TAIR").

In particular, the invention relates to the use as defined above, in which said miR164a has a nucleotide sequence having at least 80% identity, preferably at least 90% identity, with the nucleotide sequence SEQ ID NO: 1.

In an embodiment, the invention relates to the use as defined above, in which said miPEP is miPEP164a, in particular in which said miPEP164a has an amino acid sequence consisting of the sequence SEQ ID NO: 2.

In particular, the invention relates to the use as defined above, in which said miPEP164a has an amino acid sequence having at least 80% identity, preferably at least 90% identity, with the amino acid sequence SEQ ID NO: 2.

In an embodiment, the invention relates to the use as defined above, in which said gene that is involved in the development of the vegetative or reproductive parts of the plant is selected from the group consisting of: REVOLUTA (Accession No. AT5G60690), PHABULOSA (Accession No. AT2G34710), PHAVOLUTA (Accession No. AT1G30490), ATHB-8 (Accession No. AT4G32880) and ATHB-15 (Accession No. AT1G52150) (accession numbers according to the database The *Arabidopsis* Information Resource "TAIR").

In an embodiment, the invention relates to the use as defined above, in which said miRNA is miR165a, in particular in which said miR165a has a nucleotide sequence consisting of SEQ ID NO: 5.

In an embodiment, the invention relates to the use as defined above, in which said miRNA is miR165a, in particular in which said miR165a has a nucleotide sequence consisting of SEQ ID NO: 5, and said gene that is involved in the development of the vegetative or reproductive parts of the plant is selected from the group consisting of: REVOLUTA (Accession No. AT5G60690), PHABULOSA (Accession No. AT2G34710), PHAVOLUTA (Accession No. AT1G30490), ATHB-8 (Accession No. AT4G32880) and ATHB-15 (Accession No. AT1G52150) (accession numbers according to the database The *Arabidopsis* Information Resource "TAIR").

In particular, the invention relates to the use as defined above, in which said miR165a has a nucleotide sequence having at least 80% identity, preferably at least 90% identity, with the nucleotide sequence SEQ ID NO: 5.

In an embodiment, the invention relates to the use as defined above, in which said miPEP is miPEP165a, in particular in which said miPEP165a has an amino acid sequence consisting of the sequence SEQ ID NO: 6.

In particular, the invention relates to the use as defined above, in which said miPEP165a has an amino acid sequence having at least 80% identity, preferably at least 90% identity, with the amino acid sequence SEQ ID NO: 6.

In an embodiment, the invention relates to the use as defined above, in which said gene that is involved in the development of the vegetative or reproductive parts of the plant is selected from the group consisting of: TCP3 (Accession No. AT1G53230.1) and TCP4 (Accession No. AT3G15030.1) (accession numbers according to the database The *Arabidopsis* Information Resource "TAIR").

In an embodiment, the invention relates to the use as defined above, in which said miRNA is miR319a, in particular in which said miR319a has a nucleotide sequence consisting of the sequence SEQ ID NO: 9.

In an embodiment, the invention relates to the use as defined above, in which said miRNA is miR319a, in particular in which said miR319a has a nucleotide sequence consisting of SEQ ID NO: 9, and said gene that is involved in the development of the vegetative or reproductive parts of the plant is selected from the group consisting of: TCP3 (Accession No. AT1G53230.1) and TCP4 (Accession No. AT3G15030.1 (accession numbers according to the database The *Arabidopsis* Information Resource "TAIR").

In particular, the invention relates to the use as defined above, in which said miR319a has a nucleotide sequence having at least 80% identity, preferably at least 90% identity, with the nucleotide sequence SEQ ID NO: 9.

In an embodiment, the invention relates to the use as defined above, in which said miPEP is miPEP319a, in particular in which said miPEP319a has an amino acid sequence consisting of the sequence SEQ ID NO: 10.

In particular, the invention relates to the use as defined above, in which said miPEP319a has an amino acid sequence having at least 80% identity, preferably at least 90% identity, with the amino acid sequence SEQ ID NO: 10.

In an embodiment, the invention relates to the use as defined above, in which said plant is a cruciferous plant such as *Arabidopsis thaliana*, a leguminous plant such as *Glycine max* (soya), *Medicago truncatula* and *Medicago sativa* (alfalfa) or a solanaceous plant such as *Nicotiana benthamiana* (tobacco), *Solanum tuberosum* (potato), *Solanum lycopersicum* (tomato) or *Solanum melongena* (aubergine).

In an embodiment, the invention relates to the use as defined above, in which said plant is a cruciferous plant.

In an embodiment, the invention relates to the use as defined above, in which said plant is a cruciferous plant and the miRNA is miR164a.

In an embodiment, the invention relates to the use as defined above, in which said plant is a cruciferous plant and the miRNA is miR165a.

In an embodiment, the invention relates to the use as defined above, in which said plant is a cruciferous plant and the miRNA is miR319a.

In an embodiment, the invention relates to the use as defined above, in which said plant is *Arabidopsis thaliana*.

In an embodiment, the invention relates to the use as defined above, for promoting growth of an *Arabidopsis thaliana* plant, in which miPEP164a is introduced exogenously into said *Arabidopsis thaliana* plant, said miPEP164a also being present naturally in said *Arabidopsis thaliana* plant, said miPEP164a introduced exogenously being a peptide the sequence of which comprises or consists of a sequence identical to that of said miPEP164a naturally present, said sequence of the miPEP164a naturally present being encoded by an open reading frame situated at 5' on the primary transcript of the miR164a, and said miR164a regulates the expression of at least one gene involved in the development of the vegetative or reproductive parts of *Arabidopsis thaliana*, the sum of the quantity of said miPEP164a introduced exogenously and that of said miPEP164a naturally present being strictly greater than the quantity of said miPEP164a naturally present in said *Arabidopsis thaliana* plant.

In an embodiment, the invention relates to the use as defined above, for promoting the growth of an *Arabidopsis thaliana* plant, in which miPEP165a is introduced exogenously into said *Arabidopsis thaliana* plant, said miPEP165a also being present naturally in said *Arabidopsis thaliana* plant, said miPEP165a introduced exogenously being a peptide the sequence of which comprises or consists of a sequence identical to that of said miPEP165a naturally present, said sequence of the miPEP165a naturally present being encoded by an open reading frame situated at 5' on the primary transcript of the miR165a, and said miR165a regulates the expression of at least one gene involved in the development of the vegetative or reproductive parts of *Arabidopsis thaliana*, the sum of the quantity of said miPEP165a introduced exogenously and that of said miPEP165a naturally present being strictly greater than the quantity of said miPEP165a naturally present in said *Arabidopsis thaliana* plant.

In an embodiment, the invention relates to the use as defined above, for promoting the growth of an *Arabidopsis thaliana* plant, in which miPEP319a is introduced exogenously into said *Arabidopsis thaliana* plant, said miPEP319a also being present naturally in said *Arabidopsis thaliana* plant, said miPEP319a introduced exogenously being a peptide the sequence of which comprises or consists of a sequence identical to that of said miPEP319a naturally present, said sequence of the miPEP319a naturally present being encoded by an open reading frame situated at 5' on the primary transcript of the miR319a, and said miR319a regulates the expression of at least one gene involved in the development of the vegetative or reproductive parts of *Arabidopsis thaliana*, the sum of the quantity of said miPEP319a introduced exogenously and that of said miPEP319a naturally present being strictly greater than the quantity of said miPEP319a naturally present in said *Arabidopsis thaliana* plant.

In an embodiment, the invention relates to the use as defined above, in which said miPEP is introduced externally into the plant, preferably by watering, by spraying or by adding a fertilizer, a compost, a culture substrate or a support in contact with the plant.

In an embodiment, the invention relates to the use as defined above, in which said miPEP is introduced externally into a grain or seed, preferably by watering, by spraying or by adding a fertilizer, a compost, a culture substrate or a support in contact with the grain or seed.

In an embodiment, the invention relates to the method as defined above, in which said miPEP is used for treating the plant in the form of grain or seed.

In an embodiment, the invention relates to the use as defined above, in which said miPEP is introduced by watering and by spraying.

In an embodiment, the invention relates to the use as defined above, in which said miPEP is introduced by watering and by adding a fertilizer.

In an embodiment, the invention relates to the use as defined above, in which said miPEP is introduced by spraying and by adding a fertilizer.

In an embodiment, the invention relates to the use as defined above, in which said miPEP is introduced by watering, by spraying and by adding a fertilizer.

The inventors in fact found, unexpectedly, that it is possible to apply a composition comprising a miPEP directly onto the plant for modulating the accumulation of the corresponding miRNA in the plant, which indicates that the miPEP is taken up by the plant.

In an embodiment, the invention relates to the use as defined above, in which the plant is treated with a composition comprising $10^{-9}$ M to $10^{-4}$ M of said miPEP, in particular $10^{-9}$ M, $10^{-8}$ M, $10^{-7}$ M, $10^{-6}$ M, $10^{-5}$ M or $10^{-4}$ M of said miPEP.

Preferably, the compositions have a concentration from $10^{-8}$ M to $10^{-5}$ M for application by watering or by spraying on the plant.

In a complementary manner, more or less concentrated compositions can be envisaged for treating the plant with miPEP. For example, non limitatively, more concentrated compositions comprising $10^{-1}$ M to $10^{-3}$ M, in particular $10^{-2}$ M of miPEP, can be used in the case when the miPEP introduced exogenously is administered to the plant by spreading fertilizer.

The solubility properties of the miPEPs are determined in particular by their amino acid composition. The hydrophilic miPEPs can be solubilized and conditioned in aqueous solutions, such as water. The hydrophobic miPEPs can be solubilized and conditioned in solvents, such as organic solvents.

For treating plants with miPEPs, the organic solvents are solvents that are non-toxic for the plants in small quantities, i.e. they do not have harmful effects on the development of the plant. Non limitatively, the organic solvents can be selected from acetonitrile and acetic acid.

The miPEPs can also be solubilized and conditioned in mixtures of organic solvents, for example a mixture of acetonitrile and acetic acid. In particular, the miPEPs can be solubilized in a solution comprising 50% acetonitrile, 10% acetic acid and 40% water (volume/volume/volume).

In particular, the miPEP164a is solubilized in water.

In particular, the miPEP164a is at a concentration from $10^{-9}$ M to $10^{-4}$ M in water.

In particular, the miPEP165a is solubilized in water.

In particular, the miPEP165a is at a concentration from $10^{-9}$ M to $10^{-4}$ M in water.

In particular, the miPEP319a is solubilized in a solution comprising 50% acetonitrile, 10% acetic acid and 40% water (volume/volume/volume).

In particular, the miPEP319a, solubilized in a solution comprising 50% acetonitrile, 10% acetic acid and 40% water (volume/volume/volume), is diluted to a concentration from $10^{-9}$ M to $10^{-4}$ M with water.

In an embodiment, the invention relates to the use as defined above, in which said miPEP is introduced into the plant by means of a nucleic acid encoding for said miPEP, said nucleic acid being introduced into the plant.

In an embodiment, the invention relates to the use as defined above, in which the size of the stem is increased in the plant into which said miPEP has been introduced relative to the size of the stem of an identical plant of the same age, into which a miPEP has not been introduced, or relative to the size of the stem of an identical plant of the same age, into which said miPEP has not been introduced.

In an embodiment, the invention relates to the use as defined above, in which the number of leaves is increased in the plant into which said miPEP has been introduced relative to the number of leaves of an identical plant of the same age, into which a miPEP has not been introduced, or relative to the number of leaves of an identical plant of the same age, into which said miPEP has not been introduced.

In an embodiment, the invention relates to the use as defined above, in which the size of the leaves is increased in the plant into which said miPEP has been introduced relative to the size of the leaves of an identical plant of the same age, into which a miPEP has not been introduced, or relative to the size of the leaves of an identical plant of the same age, into which said miPEP has not been introduced.

In an embodiment, the invention relates to the use as defined above, in which the number of roots is increased in the plant into which said miPEP has been introduced relative to the number of roots of an identical plant of the same age, into which a miPEP has not been introduced, or relative to the number of roots of an identical plant of the same age, into which said miPEP has not been introduced.

In an embodiment, the invention relates to the use as defined above, in which the length of the roots is increased in the plant into which said miPEP has been introduced relative to the length of the roots of an identical plant of the same age, into which a miPEP has not been introduced, or relative to the length of the roots of an identical plant of the same age, into which said miPEP has not been introduced.

In an embodiment, the invention relates to the use as defined above, in which the number of flowers is increased in the plant into which said miPEP has been introduced relative to the number of flowers of an identical plant of the same age, into which a miPEP has not been introduced, or relative to the number of flowers of an identical plant of the same age, into which said miPEP has not been introduced.

In an embodiment, the invention relates to the use as defined above, in which the date of flowering is brought forward in the plant into which said miPEP has been introduced relative to the date of flowering of an identical plant of the same age, into which a miPEP has not been introduced, or relative to the date of flowering of an identical plant of the same age, into which said miPEP has not been introduced.

In an embodiment, the invention relates to the use as defined above, in which the size of the floral stalk is increased in the plant into which said miPEP has been introduced relative to the size of the floral stalk of an identical plant of the same age, into which a miPEP has not been introduced, or relative to the size of the floral stalk of an identical plant of the same age, into which said miPEP has not been introduced.

The increase in the parameters making it possible to determine and quantify the growth in the plant into which the miPEP was introduced (such as the size of the stem, the number and size of the leaves, or also the number and length of the roots) is preferably demonstrated by comparison with an identical plant (i.e. a plant of the same species and/or variety), of the same age and grown under the same conditions, but into which a miPEP has not been introduced.

The invention also relates to the use of a miPEP introduced exogenously into a plant for promoting its growth,
said miPEP being encoded by the primary transcript, introduced into the plant artificially, of a miRNA,
said primary transcript, said miRNA and said miPEP not being present naturally in the plant,
said miPEP being capable of modulating the accumulation of said miRNA in said plant, and said miRNA regulates the expression of at least one gene involved in the development of the vegetative or reproductive parts of the plant, in particular the roots, the stem, the leaves or the flowers.

In a particular embodiment, said primary transcript of the miRNA, the miRNA and said miPEP are introduced into the plant by means of a vector.

In another aspect, the invention relates to a method for promoting plant growth, comprising a step of introducing a miPEP into a plant exogenously, said miPEP also being present naturally in said plant,
said miPEP introduced exogenously being a peptide of 3 to 100 amino acids, in particular of 4 to 100 amino acids, the sequence of which comprises or consists of a sequence identical to that of said miPEP naturally present, and said sequence of the miPEP naturally present is encoded by an open reading frame situated at 5' on the primary transcript of a miRNA, said miPEP being capable of modulating the accumulation of said miRNA, and said miRNA regulates the expression of at least one gene involved in the development of the vegetative or reproductive parts of the plant, in particular the roots, the stem, the leaves or the flowers,
the sum of the quantity of said miPEP introduced exogenously and that of said miPEP that is naturally present being strictly greater than the quantity of said miPEP naturally present.

In an embodiment, the invention relates to a method as defined above, in which said gene that is involved in the development of the vegetative or reproductive parts of the plant is selected from the group consisting of: NAC1 (Accession No. AT1G56010.1), NAC4 (Accession No. AT5G07680.1), NAC5 (Accession No. AT5G61430.1), CUC1 (Accession No. AT3G15170.1) and CUC2 (Accession No. AT5G53950.1).

In an embodiment, the invention relates to a method as defined above, in which said miRNA is miR164a, in particular in which said miR164a has a nucleotide sequence consisting of SEQ ID NO: 1.

In an embodiment, the invention relates to a method as defined above, in which said miRNA is miR164a, in particular in which said miR164a has a nucleotide sequence consisting of SEQ ID NO: 1, and said gene that is involved in the development of the vegetative or reproductive parts of the plant is selected from the group consisting of: NAC1 (Accession No. AT1G56010.1), NAC4 (Accession No. AT5G07680.1), NAC5 (Accession No. AT5G61430.1), CUC1 (Accession No. AT3G15170.1) and CUC2 (Accession No. AT5G53950.1).

In an embodiment, the invention relates to a method as defined above, in which said miPEP is miPEP164a, in particular in which said miPEP164a has an amino acid sequence consisting of SEQ ID NO: 2.

In an embodiment, the invention relates to a method as defined above, in which said gene that is involved in the development of the vegetative or reproductive parts of the plant is selected from the group consisting of: REVOLUTA (Accession No. AT5G60690), PHABULOSA (Accession No. AT2G34710), PHAVOLUTA (Accession No. AT1G30490), ATHB-8 (Accession No. AT4G32880) and ATHB-15 (Accession No. AT1G52150).

In an embodiment, the invention relates to a method as defined above, in which said miRNA is miR165a, in particular in which said miR165a has a nucleotide sequence consisting of SEQ ID NO: 5.

In an embodiment, the invention relates to a method as defined above, in which said miRNA is miR165a, in particular in which said miR165a has a nucleotide sequence consisting of SEQ ID NO: 5, and said gene that is involved in the development of the vegetative or reproductive parts of the plant is selected from the group consisting of: REVOLUTA (Accession No. AT5G60690), PHABULOSA (Accession No. AT2G34710), PHAVOLUTA (Accession No. AT1G30490), ATHB-8 (Accession No. AT4G32880) and ATHB-15 (Accession No. AT1G52150).

In an embodiment, the invention relates to a method as defined above, in which said miPEP is miPEP165a, in particular in which said miPEP165a has an amino acid sequence consisting of SEQ ID NO: 6.

In an embodiment, the invention relates to a method as defined above, in which said gene that is involved in the development of the vegetative or reproductive parts of the plant is selected from the group consisting of: TCP3 (Accession No. AT1G53230.1) and TCP4 (Accession No. AT3G15030.1).

In an embodiment, the invention relates to a method as defined above, in which said miRNA is miR319a, in particular in which said miR319a has a nucleotide sequence consisting of SEQ ID NO: 9.

In an embodiment, the invention relates to a method as defined above, in which said miRNA is miR319a, in particular in which said miR319a has a nucleotide sequence consisting of SEQ ID NO: 9, and said gene that is involved in the development of the vegetative or reproductive parts of the plant is selected from the group consisting of: TCP3 (Accession No. AT1G53230.1) and TCP4 (Accession No. AT3G15030.1).

In an embodiment, the invention relates to a method as defined above, in which said miPEP is miPEP319a, in particular in which said miPEP319a has an amino acid sequence consisting of SEQ ID NO: 10.

In an embodiment, the invention relates to a method as defined above, in which said plant is a cruciferous plant such as *Arabidopsis thaliana*, a leguminous plant such as *Glycine max* (soya), *Medicago truncatula* and *Medicago sativa* (alfalfa) or a solanaceous plant such as *Nicotiana benthamiana* (tobacco), *Solanum tuberosum* (potato), *Solanum lycopersicum* (tomato) or *Solanum melongena* (aubergine).

In an embodiment, the invention relates to a method as defined above, in which said plant is a cruciferous plant.

In an embodiment, the invention relates to a method as defined above, in which said plant is *Arabidopsis thaliana*.

In an embodiment, the invention relates to a method as defined above, in which said plant is a cruciferous plant and the miRNA is miR164a.

In an embodiment, the invention relates to a method as defined above, in which said plant is a cruciferous plant and the miRNA is miR165a.

In an embodiment, the invention relates to a method as defined above, in which said plant is a cruciferous plant and the miRNA is miR319a.

In an embodiment, the invention relates to a method as defined above, for promoting the growth of an *Arabidopsis thaliana* plant, in which miPEP164a is introduced exogenously into said *Arabidopsis thaliana* plant, said miPEP164a also being present naturally in said *Arabidopsis thaliana* plant, said miPEP164a introduced exogenously being a peptide comprising or consisting of a sequence identical to that of said miPEP164a naturally present, in which said miPEP164a naturally present is a peptide of 3 to 100, in particular of 4 to 100 amino acids, the sequence of which is encoded by an open reading frame situated at 5' on the primary transcript of the miR164a, said miPEP164a being capable of increasing the accumulation of said miR164a, in which said miR164a regulates the expression of at least one gene involved in the development of the vegetative or reproductive parts of *Arabidopsis thaliana*, the sum of the quantity of said miPEP164a introduced exogenously and that of said miPEP164a naturally present being strictly greater than the quantity of said miPEP164a naturally present.

In an embodiment, the invention relates to a method as defined above, for promoting the growth of an *Arabidopsis thaliana* plant, in which miPEP165a is introduced exogenously into said *Arabidopsis thaliana* plant, said miPEP165a also being naturally present in said *Arabidopsis thaliana* plant, said miPEP165a introduced exogenously being a peptide comprising or consisting of a sequence identical to that of said miPEP165a naturally present, in which said miPEP165a naturally present is a peptide of 3 to 100 amino acids, in particular of 4 to 100 amino acids the sequence of which is encoded by an open reading frame situated at 5' on the primary transcript of the miR165a, said miPEP165a being capable of increasing the accumulation of said miR165a, in which said miR165a regulates the expression of at least one gene involved in the development of the vegetative or reproductive parts of *Arabidopsis thaliana*, the sum of the quantity of said miPEP165a introduced exogenously and that of said miPEP165a naturally present being strictly greater than the quantity of said miPEP165a naturally present.

In an embodiment, the invention relates to a method as defined above, for promoting the growth of an *Arabidopsis thaliana* plant, in which miPEP319a is introduced exogenously into said *Arabidopsis thaliana* plant, said miPEP319a also being naturally present in said *Arabidopsis thaliana* plant, said miPEP319a introduced exogenously being a peptide comprising or consisting of a sequence identical to that of said miPEP319a naturally present, in which said miPEP319a naturally present is a peptide of 3 to 100 amino acids, in particular of 4 to 100 amino acids the sequence of which is encoded by an open reading frame situated at 5' on the primary transcript of the miR319a, said miPEP319a being capable of increasing the accumulation of said miR319a, in which said miR319a regulates the expression of at least one gene involved in the development of the vegetative or reproductive parts of *Arabidopsis thaliana*, the sum of the quantity of said miPEP319a introduced exogenously and that of said miPEP319a naturally present being strictly greater than the quantity of said miPEP319a naturally present.

In an embodiment, the invention relates to a method as defined above, in which said miPEP is introduced externally into the plant, preferably by watering, by spraying or by adding a fertilizer, a compost, a culture substrate or a support in contact with the plant.

In an embodiment, the invention relates to a method as defined above, in which said miPEP is introduced externally into the grain or seed, preferably by watering, by spraying or by adding a fertilizer, a compost, a culture substrate or a support in contact with the grain or seed.

In an embodiment, the invention relates to the method as defined above, in which said miPEP is used for treating the plant in the form of grain or seed.

In an embodiment, the invention relates to a method as defined above, in which said miPEP is administered to the plant in the form of a composition comprising $10^{-9}$ M to $10^{-4}$ M of said miPEP, in particular $10^{-9}$, $10^{-8}$, $10^{-7}$, $10^{-6}$, $10^{-5}$ or $10^{-4}$ M of said miPEP.

In an embodiment, the invention relates to a method as defined above, in which said miPEP is introduced into the plant by means of a nucleic acid encoding for said miPEP, said nucleic acid being introduced into the plant.

In an embodiment, the invention relates to a method as defined above, in which the size of the stem is increased in the plant into which said miPEP has been introduced relative to the size of the stem of an identical plant of the same age, into which a miPEP has not been introduced, or relative to the size of the stem of an identical plant of the same age, into which said miPEP has not been introduced.

In an embodiment, the invention relates to a method as defined above, in which the number of leaves is increased in the plant into which said miPEP has been introduced relative to the number of leaves of an identical plant of the same age, into which a miPEP has not been introduced, or relative to the number of leaves of an identical plant of the same age, into which said miPEP has not been introduced.

In an embodiment, the invention relates to a method as defined above, in which the size of the leaves is increased in the plant into which said miPEP has been introduced relative to the size of the leaves of an identical plant of the same age, into which a miPEP has not been introduced, or relative to the size of the leaves of an identical plant of the same age, into which said miPEP has not been introduced.

In an embodiment, the invention relates to a method as defined above, in which the number of roots is increased in the plant into which said miPEP has been introduced relative to the number of roots of an identical plant of the same age, into which a miPEP has not been introduced, or relative to the number of roots of an identical plant of the same age, into which said miPEP has not been introduced.

In an embodiment, the invention relates to a method as defined above, in which the length of the roots is increased in the plant into which said miPEP has been introduced relative to the length of the roots of an identical plant of the same age, into which a miPEP has not been introduced, or relative to the length of the roots of an identical plant of the same age, into which said miPEP has not been introduced.

In an embodiment, the invention relates to a method as defined above, in which the number of flowers is increased in the plant into which said miPEP has been introduced relative to the number of flowers of an identical plant of the same age, into which a miPEP has not been introduced, or relative to the number of flowers of an identical plant of the same age, into which said miPEP has not been introduced.

In an embodiment, the invention relates to a method as defined above, in which the date of flowering is brought forward in the plant into which said miPEP has been introduced relative to the date of flowering of an identical plant of the same age, into which a miPEP has not been introduced, or relative to the date of flowering of an identical plant of the same age, into which said miPEP has not been introduced.

In an embodiment, the invention relates to a method as defined above, in which the size of the floral stalk is increased in the plant into which said miPEP has been introduced relative to the size of the floral stalk of an identical plant of the same age, into which a miPEP has not been introduced, or relative to the size of the floral stalk of an identical plant of the same age, into which said miPEP has not been introduced.

In another aspect, the invention relates to a plant into which a miPEP has been introduced according to the use or the method for promoting plant growth described above.

In another aspect, the invention relates to a method for the production of a transgenic plant comprising:
a) a step of introducing a nucleic acid encoding for a miPEP of 3 to 100 amino acids, in particular of 4 to 100 amino acids, into a plant, or into at least one cell of said plant, under conditions allowing the expression of said miPEP, said miPEP also being naturally present in said plant, said miPEP naturally present being a peptide the sequence of which is encoded by an open reading frame situated at 5' on the primary transcript of a miRNA, said miPEP being capable of modulating the accumulation of said miRNA in the plant, in which said miRNA regulates the expression of at least one gene involved in the development of the vegetative or reproductive parts of the plant, in particular the roots, the stem, the leaves or the flowers, and
b) a step of growing the plant, or at least one cell of said plant, obtained in step a) under conditions allowing a transgenic plant to be obtained.

In an embodiment, the invention relates to a method for the production of a transgenic plant as defined above, in which said transgenic plant obtained in step b) has improved growth relative to an identical plant, into which said nucleic acid has not been introduced.

In an embodiment, the invention relates to a method for the production of a transgenic plant as defined above, in which step a) is carried out using a vector containing said nucleic acid, preferably a plasmid.

In an embodiment, the invention relates to a method for the production of a transgenic plant as defined above, in which said nucleic acid does not comprise the complete sequence of said miRNA.

In an embodiment, the invention relates to a method for the production of a transgenic plant as defined above, in which the expression of said nucleic acid from step a) is put under the control of a strong promoter, preferably a constitutive strong promoter such as the promoter 35S.

In an embodiment, the invention relates to a method for the production of a transgenic plant as defined above, in which said gene that is involved in the development of the vegetative or reproductive parts of the plant is selected from the group consisting of: NAC1 (Accession No. AT1G56010.1), NAC4 (Accession No. AT5G07680.1), NAC5 (Accession No. AT5G61430.1), CUC1 (Accession No. AT3G15170.1) and CUC2 (Accession No. AT5G53950.1).

In an embodiment, the invention relates to a method for the production of a transgenic plant as defined above, in which said miRNA is miR164a, in particular in which said miR164a has a nucleotide sequence consisting of SEQ ID NO: 1.

In an embodiment, the invention relates to a method for the production of a transgenic plant as defined above, in which said miRNA is miR164a, in particular in which said miR164a has a nucleotide sequence consisting of SEQ ID NO: 1, and said gene that is involved in the development of the vegetative or reproductive parts of the plant is selected from the group consisting of: NAC1 (Accession No. AT1G56010.1), NAC4 (Accession No. AT5G07680.1), NAC5 (Accession No. AT5G61430.1), CUC1 (Accession No. AT3G15170.1) and CUC2 (Accession No. AT5G53950.1).

In an embodiment, the invention relates to a method for the production of a transgenic plant as defined above, in which said miPEP is miPEP164a, in particular in which said miPEP164a has an amino acid sequence consisting of SEQ ID NO: 2.

In an embodiment, the invention relates to a method for the production of a transgenic plant as defined above, in which said nucleic acid introduced in step a) comprises a nucleotide sequence consisting of SEQ ID NO: 3.

In an embodiment, the invention relates to a method for the production of a transgenic plant as defined above, in which said gene that is involved in the development of the vegetative or reproductive parts of the plant is selected from the group consisting of: REVOLUTA (Accession No. AT5G60690), PHABULOSA (Accession No. AT2G34710), PHAVOLUTA (Accession No. AT1G30490), ATHB-8 (Accession No. AT4G32880) and ATHB-15 (Accession No. AT1G52150).

In an embodiment, the invention relates to a method for the production of a transgenic plant as defined above, in which said miRNA is miR165a, in particular in which said miR165a has a nucleotide sequence consisting of SEQ ID NO: 5.

In an embodiment, the invention relates to a method for the production of a transgenic plant as defined above, in which said miRNA is miR165a, in particular in which said miR165a has a nucleotide sequence consisting of SEQ ID NO: 5, and said gene that is involved in the development of the vegetative or reproductive parts of the plant is selected from the group consisting of: REVOLUTA (Accession No. AT5G60690), PHABULOSA (Accession No. AT2G34710), PHAVOLUTA (Accession No. AT1G30490), ATHB-8 (Accession No. AT4G32880) and ATHB-15 (Accession No. AT1G52150).

In an embodiment, the invention relates to a method for the production of a transgenic plant as defined above, in which said miPEP is miPEP165a, in particular in which said miPEP165a has an amino acid sequence consisting of SEQ ID NO: 6.

In an embodiment, the invention relates to a method for the production of a transgenic plant as defined above, in which said nucleic acid introduced in step a) comprises a nucleotide sequence consisting of SEQ ID NO: 7.

In an embodiment, the invention relates to a method for the production of a transgenic plant as defined above, in which said gene that is involved in the development of the vegetative or reproductive parts of the plant is selected from the group consisting of: TCP3 (Accession No. AT1G53230.1) and TCP4 (Accession No. AT3G15030.1).

In an embodiment, the invention relates to a method for the production of a transgenic plant as defined above, in which said miRNA is miR319a, in particular in which said miR319a has a nucleotide sequence consisting of SEQ ID NO: 9.

In an embodiment, the invention relates to a method for the production of a transgenic plant as defined above, in which said miRNA is miR319a, in particular in which said miR319a has a nucleotide sequence consisting of SEQ ID NO: 9, and said gene that is involved in the development of the vegetative or reproductive parts of the plant is selected from the group consisting of: TCP3 (Accession No. AT1G53230.1) and TCP4 (Accession No. AT3G15030.1).

In an embodiment, the invention relates to a method for the production of a transgenic plant as defined above, in which said miPEP is miPEP319a, in particular in which said miPEP319a has an amino acid sequence consisting of SEQ ID NO: 10.

In an embodiment, the invention relates to a method for the production of a transgenic plant as defined above, in which said nucleic acid introduced in step a) comprises a nucleotide sequence consisting of SEQ ID NO: 11.

In an embodiment, the invention relates to a method for the production of a transgenic plant as defined above, in which said transgenic plant is a cruciferous plant such as *Arabidopsis thaliana*, a leguminous plant such as *Glycine max* (soya), *Medicago truncatula* and *Medicago sativa* (alfalfa) or a solanaceous plant such as *Nicotiana benthamiana* (tobacco), *Solanum tuberosum* (potato), *Solanum lycopersicum* (tomato) or *Solanum melongena* (aubergine).

In an embodiment, the invention relates to a method for the production of a transgenic plant as defined above, in which said transgenic plant is a cruciferous plant.

In an embodiment, the invention relates to a method for the production of a transgenic plant as defined above, in which said transgenic plant is *Arabidopsis thaliana*.

In an embodiment, the invention relates to a method for the production of a transgenic plant as defined above, comprising:

a) a step of introducing a nucleic acid containing the nucleotide sequence SEQ ID NO: 3, encoding for miPEP164a, consisting of the amino acid sequence SEQ ID NO: 2, in an *Arabidopsis thaliana* plant, or in at least one cell of said *Arabidopsis thaliana* plant, under conditions allowing the expression of miPEP164a, said miPEP164a also being naturally present in said *Arabidopsis thaliana* plant, said miPEP naturally present being a peptide the sequence of which is encoded by an open reading frame situated at 5' on the primary transcript of the miR164a, said miPEP164a being capable of modulating the accumulation of said miR164, in which said miR164a regulates the expression of at least one gene involved in the development of the vegetative or reproductive parts of *Arabidopsis thaliana*, and b) a step of growing the plant, or at least one cell of said plant, obtained in step a) in conditions allowing a transgenic *Arabidopsis thaliana* plant to be obtained.

In an embodiment, the invention relates to a method for the production of a transgenic plant as defined above, comprising:

a) a step of introducing a nucleic acid containing the nucleotide sequence SEQ ID NO: 7, encoding for miPEP165a consisting of the amino acid sequence SEQ ID NO: 6, in an *Arabidopsis thaliana* plant, or in at least one cell of said *Arabidopsis thaliana* plant, in conditions allowing the expression of miPEP165a, said miPEP165a also being naturally present in said *Arabidopsis thaliana* plant, said miPEP naturally present being a peptide the sequence of which is encoded by an open reading frame situated at 5' on the primary transcript of the miR165a, said miPEP165a being capable of modulating the accumulation of said miR165a, in which said miR165a regulates the expression of at least one gene involved in the development of the vegetative or reproductive parts of *Arabidopsis thaliana*, and b) a step of growing the plant, or at least one cell of said plant, obtained in step a) under conditions allowing a transgenic *Arabidopsis thaliana* plant to be obtained.

In an embodiment, the invention relates to a method for the production of a transgenic plant as defined above, comprising:

a) a step of introducing a nucleic acid containing the nucleotide sequence SEQ ID NO: 11, encoding for miPEP319a consisting of the amino acid sequence SEQ ID NO: 10, in an *Arabidopsis thaliana* plant, or in at least one cell of said *Arabidopsis thaliana* plant, under conditions allowing the expression of miPEP319a, said miPEP319a also being naturally present in said *Arabidopsis thaliana* plant, said miPEP naturally present being a peptide the sequence of which is encoded by an open reading frame situated at 5' on the primary transcript of the miR319a, said miPEP319a being capable of modulating the accumulation of said miR319a, in which said miR319a regulates the expression of at least one gene involved in the development of the vegetative or reproductive parts of *Arabidopsis thaliana*, and b) a step of growing the plant, or at least one cell of said plant, obtained in step a) under conditions allowing a transgenic *Arabidopsis thaliana* plant to be obtained.

In an embodiment, the invention relates to a production method as defined above, in which said miPEP is introduced into the plant by means of a nucleic acid encoding for said miPEP, said nucleic acid being introduced into the plant.

In an embodiment, the invention relates to a method for the production of a transgenic plant as defined above, in which the size of the stem is increased in the plant into which said miPEP has been introduced relative to the size of the stem of an identical plant of the same age, into which a miPEP has not been introduced, or relative to the size of the stem of an identical plant of the same age, into which said miPEP has not been introduced.

In an embodiment, the invention relates to a method for the production of a transgenic plant as defined above, in which the number of leaves is increased in the plant into which said miPEP has been introduced relative to the number of leaves of an identical plant of the same age, into which a miPEP has not been introduced, or relative to the number of leaves of an identical plant of the same age, into which said miPEP has not been introduced.

In an embodiment, the invention relates to a method for the production of a transgenic plant as defined above, in which the size of the leaves is increased in the plant into which said miPEP has been introduced relative to the size of the leaves of an identical plant of the same age, into which a miPEP has not been introduced, or relative to the size of the leaves of an identical plant of the same age, into which said miPEP has not been introduced.

In an embodiment, the invention relates to a method for the production of a transgenic plant as defined above, in which the number of roots is increased in the plant into which said miPEP has been introduced relative to the number of roots of an identical plant of the same age, into which a miPEP has not been introduced, or relative to the number of roots of an identical plant of the same age, into which said miPEP has not been introduced.

In an embodiment, the invention relates to a method for the production of a transgenic plant as defined above, in which the length of the roots is increased in the plant into which said miPEP has been introduced relative to the length of the roots of an identical plant of the same age, into which a miPEP has not been introduced, or relative to the length of the roots of an identical plant of the same age, into which said miPEP has not been introduced.

In an embodiment, the invention relates to a method for the production of a transgenic plant as defined above, in which the number of flowers is increased in the plant into which said miPEP has been introduced relative to the number of flowers of an identical plant of the same age, into which a miPEP has not been introduced, or relative to the number of flowers of an identical plant of the same age, into which said miPEP has not been introduced.

In an embodiment, the invention relates to a method for the production of a transgenic plant as defined above, in which the date of flowering is brought forward in the plant into which said miPEP has been introduced relative to the date of flowering of an identical plant of the same age, into which a miPEP has not been introduced, or relative to the date of flowering of an identical plant of the same age, into which said miPEP has not been introduced.

In an embodiment, the invention relates to a method for the production of a transgenic plant as defined above, in which the size of the floral stalk is increased in the plant into which said miPEP has been introduced relative to the size of the floral stalk of an identical plant of the same age, into which a miPEP has not been introduced, or relative to the size of the floral stalk of an identical plant of the same age, into which said miPEP has not been introduced.

In one aspect, the invention also relates to a transgenic plant as obtained by the production method as defined above.

In another aspect, the invention relates to a plant into which a miPEP has been introduced according to the use or the method for promoting the development of the vegetative or reproductive parts of the plant.

In another aspect, the invention relates to a composition, in particular a phytosanitary composition, comprising miPEP164a as the active ingredient, said miPEP164a preferably consisting of SEQ ID NO: 1.

In another aspect, the invention relates to a composition, in particular a phytosanitary composition, comprising miPEP165a as the active ingredient, said miPEP165a preferably consisting of SEQ ID NO: 5.

In another aspect, the invention relates to a composition, in particular a phytosanitary composition, comprising miPEP319a as the active ingredient, said miPEP319a preferably consisting of SEQ ID NO: 9.

In another aspect, the invention relates to a composition as defined above, in which said miPEP164a is at a concentration from $10^{-9}$ M to $10^{-4}$ M, in particular $10^{-9}$, $10^{-8}$, $10^{-7}$, $10^{-6}$, $10^{-5}$ or $10^{-4}$ M.

Preferably, a composition as defined above has a concentration from $10^{-8}$ M to $10^{-5}$ M for application by watering or by spraying on the plant.

In a complementary manner, more or less concentrated compositions can be envisaged for treating the plant with the miPEP. For example, non limitatively, more concentrated compositions comprising $10^{-1}$ M to $10^{-3}$ M, in particular $10^{-2}$ M of the miPEP, can be used in the case when the miPEP introduced exogenously is administered to the plant by spreading fertilizer.

In another aspect, the invention relates to a composition as defined above, further comprising an excipient, a diluent or a solvent.

In an embodiment, the invention relates to a composition as defined above, formulated so as to form a coating.

In another aspect, the invention relates to a composition comprising, in combination, a quantity of seeds from a plant and a quantity of a peptide the sequence of which comprises or consists of a sequence identical to that of a miPEP naturally present in said plant.

In an embodiment, the invention relates to a composition comprising, in combination, a quantity of seeds from a cruciferous plant, in particular *A. thaliana*, and a quantity of a peptide the sequence of which comprises or consists of a sequence identical to that of miPEP164a.

In an embodiment, the invention relates to a composition comprising, in combination, a quantity of seeds from a cruciferous plant, in particular *A. thaliana*, and a quantity of a peptide the sequence of which comprises or consists of a sequence identical to that of miPEP165a.

In an embodiment, the invention relates to a composition comprising, in combination, a quantity of seeds from a cruciferous plant, in particular *A. thaliana*, and a quantity of a peptide the sequence of which comprises or consists of a sequence identical to that of miPEP319a.

In another aspect, the invention relates to a composition as defined above, further comprising an excipient, a diluent or a solvent.

In an embodiment, the invention relates to a composition as defined above, formulated so as to form a coated seed.

Coating can be carried out by the methods used conventionally in the agri-food industry and can be obtained using a material capable of disintegrating in a solvent or in soil, such as a binder or clay.

According to the invention, coating can be used for example for imparting particular properties to a miPEP composition, or to a composition of seeds in combination with a miPEP.

In another aspect, the invention relates to a protocol for the production of a recombinant peptide, the sequence of which comprises or consists of a sequence identical to that of a miPEP as defined above, comprising a step of transforming an organism with an expression vector encoding for said recombinant peptide.

In an embodiment, said organism is selected from the group comprising bacteria, yeasts, fungi (other than yeasts), animal cells, plants and animals.

In an embodiment, said organism is *Escherichia coli*.

In particular, the invention relates to a protocol for the production of a recombinant peptide as defined above, comprising the following steps:
 the nucleic acid encoding said recombinant peptide is bound to a nucleic acid encoding a tag, such as GST,
 the expression vector containing said nucleic acid encoding said recombinant peptide is introduced into the bacterium *E. coli*,
 the bacterium *E. coli* containing the expression vector is cultured in LB medium preferably up to an OD between 0.2 and 0.4,
 production of the recombinant peptide is induced with IPTG, preferably for 4 to 5 hours,
 the *E. coli* bacteria are centrifuged and lysed,
 the supernatant is filtered,
 said recombinant peptide is purified on a glutathione sepharose affinity column,
 if necessary, cleaving of GST with a protease.

In another aspect, the invention relates to an antibody specifically recognizing miPEP164a, in particular said miPEP164a consisting of SEQ ID NO: 2.

In another aspect, the invention relates to an antibody specifically recognizing miPEP165a, in particular said miPEP165a consisting of SEQ ID NO: 6.

In another aspect, the invention relates to an antibody specifically recognizing miPEP319a, in particular said miPEP319a consisting of SEQ ID NO: 10.

Such an antibody can be obtained by a method known to a person skilled in the art, for example by injecting said miPEP164a into a non-human animal in order to trigger an immunization reaction and the production of antibodies by said animal.

In another aspect, the invention relates to a method for the immunolocalization of miPEP164a comprising a step of labelling a biological sample from a plant with an antibody specifically recognizing said miPEP164a.

In another aspect, the invention relates to a method for the immunolocalization of miPEP165a comprising a step of labelling a biological sample from a plant with an antibody specifically recognizing said miPEP165a.

In another aspect, the invention relates to a method for the immunolocalization of miPEP319a comprising a step of labelling a biological sample from a plant with an antibody specifically recognizing said miPEP319a.

The sequences of miPEP164a, of its open reading frame, of miR164a and of the primary transcripts of miR164a in *Arabidopsis thaliana* are shown in Table 1.

TABLE 1

| miR164a | uggagaagcagggcacgugca | SEQ ID NO: 1 |
|---|---|---|
| miPEP164a | MPSWHGMVLLPYVKHTHASTHTHTHNIYGC ACELVFH | SEQ ID NO: 2 |
| miORF164a | ATGCCATCATGGCATGGTATGGTTCTTTTGC CTTACGTAAAACACACTCACGCCAGCACAC ACACACACACACATAACATATACGGATGTG CGTGTGAGCTAGTCTTCCATTAA | SEQ ID NO: 3 |
| pri-miR164a | AGACAAGCCCCCACACTAAAAAAACAGTAA TATGGAATAAAAAAAAGCTTTCAAAACTTA GCAGTTATTAGACAAGGTATTGTTTGGCCCT AGCTAGCGATCGTTTAGCTCTCTTCACTCTC TCACTTTTTTAGTTCAACCCTTCTTTTGCGTG AGATGCCATCATGGCATGGTATGGTTCTTTT GCCTTACGTAAAACACACTCACGCCAGCAC ACACACACACACATAACATATACGGATG TGCGTGTGAGCTAGTCTTCCATTAATGCAAT CTTTGGGCCTATATATACAAACCTTTCCATA ACCAAAGTTCTCATACTACAAACGCCCCTC ATGTGCTTGGAAATGCGGGTGAGAATCTCC ATGTTGGAGAAGCAGGGCACGTGCAAACCA ACAAACACGAAATCCGTCTCATTTGCTTATT TGCACGTACTTAACTTCTCCAACATGAGCTC TTCACCC | SEQ ID NO: 4 |

The sequences of miPEP165a, of its open reading frame, of miR164a and of the primary transcripts of miR165a in *Arabidopsis thaliana* are shown in Table 2.

TABLE 2

| miR165a | ucggaccaggcuucaucccc | SEQ ID NO: 5 |
|---|---|---|
| miPEP165a | MRVKLFQLRGMLSGSRIL | SEQ ID NO: 6 |
| miORF165a | ATGAGGGTTAAGCTATTTCAGTTGAGGGGA ATGTTGTCTGGATCGAGGATATTATAG | SEQ ID NO: 7 |
| pri-miR165a | CTAGGGTTTAGGAATGACGACCTGTTTCTGT TGTGTCTTATTAAAAGCCCATCTTCGTCTCC GCCACTCATCATTCCCTCATCATAACACCAT CATCACCATTCACCAACCTCTCTCTCTCTCT CCTCTATCACTCTCTACAACAAAAATTTGTG AATCTGCTAAGATCGATTATCATGAGGGTT AAGCTATTTCAGTTGAGGGGAATGTTGTCT GGATCGAGGATATTATAGATATATACATGT GTATGTTAATGATTCAAGTGATCATAGAGA GTATCCTCGGACCAGGCTTCATCCCCCCCAA CATGTTATTGCCTCTGATCACCATTTATTGT TACATTTTTTTTGTTAATTACTTGCGCAAA TTACAAAAGCTTGGTTTTTGTGATGACTTTG AATCTTTCTTGCATGGCTTCTTAAGAGTAGA TTTACGGATCCGTCTATGCTTTTTGCTTTTTG TTTCGTTTATTTGTATTTAAAC | SEQ ID NO: 8 |

The sequences of miPEP319a, of its open reading frame, of miR319a and of the primary transcripts of miR319a in *Arabidopsis thaliana* are shown in Table 3.

TABLE 3

| miR319a | uuggacugaagggagcucccu | SEQ ID NO: 9 |
|---|---|---|
| miPEP319a | MNIHTYHHLLFPSLVFHQSSDVPNALSLHIHT YEYIIVVIDPFRITLAFR | SEQ ID NO: 10 |
| miORF319a | ATGAATATACATACATACCATCATCTTCTTT TCCCATCTCTAGTTTTTCATCAATCTTCTGAT GTTCCAAACGCTCTATCTCTTCATATACATA CATACGAATATATTATTGTTGTCATAGATCC ATTTAGAATCACTTTAGCTTTTAGATGA | SEQ ID NO: 11 |
| pri-miR319a | TTGTATCCGCAGTGTATTTCCTCGCATCTAC CATCCCTTTTCTACGCCTCTCTCCCTCTCTCT CTTTCTCCATCAAATCTTGTTTTGTTCAAAC TCTCTCTCTCATCTATTCTCTCCATACAAT ACATGAATATACATACATACCATCATCTTCT TTTCCCATCTCTAGTTTTTCATCAATCTTCTG ATGTTCCAAACGCTCTATCTCTTCATATACA TACATACGAATATATTATTGTTGTCATAGAT CCATTTAGAATCACTTTAGCTTTTAGATGAG ATCTAGGGTTTCTTTGTTTTCTTTCAAATTTT GTTGCATATTCTTCTAAATCATGGTTTTTCG CTTGCTAGGTTATAGATCCATGCAAATATG GAGTAGATGTACAAACACACGCTCGGACGC ATATTACACATGTTCATACACTTAATACTCG CTGTTTTGAATTGATGTTTTAGGAATATATA TGTAGAGAGAGCTTCCTTGAGTCCATTCAC AGGTCGTGATATGATTCAATTAGCTTCCGAC TCATTCATCCAAATACCGAGTCGCCAAAAT TCAAACTAGACTCGTTAAATGAATGAATGA TGCGGTAGACAAATTGGATCATTGATTCTCT TTGATTGGACTGAAGGGAGCTCCCTCT | SEQ ID NO: 12 |

Application FR 13 60727 relates to micropeptides (peptides encoded by microRNAs "miPEPs") and use thereof for modulating, gene expression.

microRNAs (miRNAs) are small non-encoding RNAs, of about 21 nucleotides after maturation, which control the expression of target genes at the post-transcriptional level, by degrading the target mRNA or by inhibiting translation thereof The miRNAs are found in plants and animals.

The target genes are often key genes in developmental processes. They encode, for example, transcription factors or proteins of the proteasome.

Very little is known about the regulation of expression of miRNAs. but in particular it is known that the latter involves, like most encoding genes, an RNA polymerase II: this enzyme produces a primary transcript, called "pri-miRNA", which is then matured by a protein complex in particular containing the enzymes of the Dicer type. This maturation leads firstly to formation of a precursor of miRNA called "pre-miRNA", having a secondary structure in stem-and-loop form containing the miRNA and its complementary sequence miRNA*. Then the precursor is matured, which leads to formation of a shorter double-stranded RNA containing the miRNA and the miRNA*. The miRNA then comes under the control of the RISC complex, which cleaves the mRNA of the target gene or inhibits its translation.

Moreover, it has been shown that the presence of introns in the primary transcript of the microRNA increases expression of the mature microRNA (Schwab el al., EMBO Rep., 14(7):615-21, 2013). However, owing to experimental difficulties, the primary transcripts of microRNAs, or pri-miRNAs, have received very little study.

About 50% of eukaryotic genes have, within their region 5'UTR (5' UnTranslated Region) upstream of the encoding sequence, small open reading frames. These small open reading frames (or "uORFs" for upstream ORFs) can play a role as regulator of translation, mainly in cis, by modulating the binding and the rate of the ribosomes on the mRNA, but also in trans according to a mechanism that is still unknown, by means of peptides encoded by said uORFs (Combier el at., Gene Dev. 22:1549-1559, 2008). By definition, the uORFS are present upstream of encoding genes.

Small ORFs have also recently been discovered in long non-encoding RNAs between genes (lincRNAs), the putative function of which, if any, is unknown (Ingolia et al., Cell, 147(4): 789-802, 2011: Guttman & Rinn, Nature, 482(7385):339-46, 2012).

However, no example has yet been reported concerning the existence of ORFs encoding peptides within non-encoding microRNAs. Until now, microRNAs, and by extension their primary transcript, have always been regarded, owing to their particular mode of action, as non-encoding regulatory RNAs that do not produce any peptide.

One of the aspects of the subject-matter of application FR 13 60727 is to propose peptides capable of modulating the expression of microRNAs.

Another aspect of the subject-matter of application FR 13 60727 is to propose a means for modulating the expression of one or more target genes of a microRNA. The subject-matter of application FR 13 60727 offers the advantage of allowing easier and more efficient control of the expression of genes targeted by the microRNAs, using a means other than microRNA.

The subject-matter of application FR 13 60727 thus relates to a method for detecting and identifying a micropeptide (miPEP) encoded by a nucleotide sequence contained in the sequence of the primary transcript of a microRNA. comprising:
  a) a step of detecting an open reading frame of 15 to 303 nucleotides contained in the sequence of the primary transcript of said microRNA, then
  b) a step of comparison between:
    the accumulation of said microRNA in a specified eukaryotic cell expressing said microRNA,
    in the presence of a peptide encoded by a nucleotide sequence that is identical or degenerated relative to that of said open reading frame, said peptide being present in the cell independently of the transcription of the primary transcript of said microRNA, and
    the accumulation of said microRNA in a eukaryotic cell of the same type as the aforesaid specified eukaryotic cell expressing said microRNA, in the absence of said peptide,
  in which a modulation of the accumulation of said microRNA in the presence of said peptide relative to the accumulation of said microRNA in the absence of said peptide indicates the existence of a micropeptide encoded by said open reading frame.

In a first step, the method for detecting and identifying a micropeptide therefore consists of detecting, on the primary transcript of a microRNA. the existence of an open reading frame potentially encoding a peptide.

The second step, in its turn, makes it possible to characterize said peptide, i.e. to determine whether said peptide corresponds to a peptide really produced in the cell, by searching for an effect of said peptide on the accumulation of said microRNA.

In order to detect an effect of the peptide on the accumulation of the microRNA, a large quantity of peptide is introduced into a first cell expressing said microRNA. The accumulation of the microRNA in this first cell is then measured and compared with the accumulation of the microRNA in a second cell identical to the first, but not containing said peptide.

Observation of a change in the quantities of microRNA between the cells in the presence and in the absence of the peptide thus indicates (i) that there is a peptide encoded on the primary transcript of said microRNA, (ii) that the sequence of this peptide is encoded by the open reading frame identified on the primary transcript of said microRNA, and (iii) that said peptide acts upon the accumulation of said microRNA.

The subject-matter of application FR 13 60727 is therefore based on the unexpected dual observation made by the inventors, that on the one hand there are open reading frames capable of encoding micropeptides present on the primary transcripts of microRNAs, and on the other hand that said micropeptides are capable of modulating the accumulation of said microRNAs.

In application FR 13 60727, the terms "microRNA", "non-encoding microRNA" and "miRNA" are equivalent and can he used interchangeably. They define small RNA molecules of about 21 nucleotides, which are not translated and do not lead to a peptide or a protein.

However, in this mature form, the microRNAs perform a function of regulation of certain genes by post-transcriptional mechanisms, for example via the RISC complex.

The primary transcript of the microRNA or "pri-miRNA" corresponds for its part to the RNA molecule directly obtained from transcription of the DNA molecule. Generally, this primary transcript undergoes one or more post-transcriptional modifications, which lead for example to a particular structure of the RNA or cleavage of certain parts of the RNA by splicing phenomena, and which lead to the precursor form of the microRNA or "pre-miRNA", then to the mature form of the microRNA or "miRNA".

The terms "micropeptides" and "miPEPs" (microRNA encoded PEPtides) are equivalent and can be used interchangeably. They define a peptide that is encoded by an open reading frame present on the primary transcript of a microRNA, and which is capable of modulating the accumulation of said microRNA. The micropeptides in the sense of application FR 13 60727 should not be understood as necessarily being peptides of small size, as "micro" does not correspond to the size of the peptide.

Taking into account the degeneration of the genetic code, one and the same micropeptide can be encoded by several nucleotide sequences. Such nucleotide sequences, differing from one another by at least one nucleotide but encoding one and the same peptide, are called "degenerated sequences".

The terms "open reading frame" or "ORF" are equivalent and can be used interchangeably. They correspond to a nucleotide sequence in a DNA or RNA molecule that can potentially encode a peptide or a protein: said open reading frame begins with a start codon, followed by a series of codons, and ends with a stop codon. In application FR 13 60727, the ORFs can be called specifically "miORFs" when the latter are present on the primary transcripts of microRNA.

In application FR 13 60727, by "accumulation" is meant the production of a molecule, such as a microRNA or a micropeptide, in the cell. Thus, "modulation" of the accumulation of a molecule in a cell corresponds to a change in the quantity of this molecule present in the cell.

In an embodiment, the subject-matter of application FR 13 60727 relates to a method for detecting and identifying a miPEP as defined above, in which the modulation of the accumulation of said microRNA is a decrease or an increase in the accumulation of said microRNA, in particular an increase.

A "decrease in the accumulation" corresponds to a lowering of the quantity of said molecule in the cell. Conversely, an "increase in the accumulation" corresponds to an increase in the quantity of said molecule in the cell.

In an advantageous embodiment, the subject-matter of application FR 13 60727 relates to a method for detecting and identifying a miPEP as defined above, in which the modulation of the accumulation of said microRNA is an increase in the accumulation of said microRNA.

In an embodiment, the subject-matter of application FR 13 60727 relates to a method for detecting and identifying a miPEP as defined above, in which the presence of said peptide in the cell results from:
  the introduction of a nucleic acid encoding said peptide into the cell, or
  the introduction of said peptide into the cell In order to characterize a miPEP, it is necessary to have a cellular model expressing a microRNA, in which said peptide to be tested is present. For this, it is possible to introduce a peptide into the cell, either by bringing the cell into contact with said peptide, or by introducing a nucleic acid encoding said peptide into the cell, and said nucleic acid will then be translated into a peptide within the cell.

In an embodiment, the subject-matter of application FR 13 60727 relates to a method for detecting and identifying a miPEP as defined above, in which said open reading frame in step a) is contained in the 5' or 3' part of said primary transcript of the microRNA. preferably in the 5' part.

The 5' or 3' parts of the primary transcript of the microRNA correspond to the terminal parts of the RNA molecule, which are cleaved during maturation of the microRNA.

In an embodiment, the subject-matter of application FR 13 60727 relates to a method for detecting and identifying a miPEP as defined above, in which said microRNA is present in a wild-type plant cell.

In application FR 13 60727, a wild-type plant cell corresponds to a plant cell that has not been genetically modified by man.

In an embodiment, the subject-matter of application FR 13 60727 relates to a method for detecting and identifying a miPEP as defined above, in which said specified eukaryotic cell, and said eukaryotic cell of the same type as the aforesaid specified eukaryotic cell, used in step b, are plant cells, preferably cells of Medicago truncatula or of Arabidopsis thaliana.

In the method for detecting and identifying a micropeptide as defined above, after identifying an ORF capable of encoding a peptide on the primary transcript of a microRNA, it is necessary to have a cellular model possessing said microRNA and said peptide, so as to be able to demonstrate a possible effect of the peptide on said microRNA.

Two options are therefore conceivable:
  the cellular model in which the miORF has been identified and that in which the effect of the peptide on the miRNA is demonstrated are identical, or
  the cellular model in which the miORF has been identified and that in which the effect of the peptide on the miRNA is demonstrated are different.

In the first option, the cellular model used for observing an effect of the peptide is the same as that in which the primary transcript of said microRNA was isolated. In this cellular model, the specified eukaryotic cells contain said microRNA naturally and only the peptide to be tested has to be introduced into these cells. In this context, said microRNA is described as "of endogenous origin" as the latter exists naturally in the cells. Nevertheless, in a cell, other copies of a microRNA of endogenous origin can be added, for example by introducing a vector encoding said microRNA of endogenous origin into the cell.

In the second option, the cellular model used for observing an effect of the peptide is different from that in which the primary transcript of said microRNA was isolated. In this cellular model, the specified eukaryotic cells contain neither the microRNA, nor the peptide to be tested. These two elements must therefore be introduced into these cells. In this context, said microRNA is described as "of exogenous origin" as the latter does not exist naturally in the cells.

In an embodiment, the subject-matter of application FR 13 60727 relates to a method for detecting and identifying a miPEP as defined above, in which said microRNA is of endogenous origin in said eukaryotic cell and in said eukaryotic cell of the same type as the aforesaid specified eukaryotic cell used in step b).

In an embodiment, the subject-matter of application FR 13 60727 relates to a method for detecting and identifying a miPEP as defined above in which said microRNA is of exogenous origin in said eukaryotic cell and in said eukaryotic cell of the same type as the aforesaid specified eukaryotic cell, used in step b), said eukaryotic cells containing a vector allowing the expression of said microRNA.

In an embodiment, the subject-matter of application FR 13 60727 relates to a method for detecting and identifying a miPEP as defined above, in which the accumulation of said microRNA is determined using quantitative RT-PCR or Northern blot.

In an embodiment, the subject-matter of application FR 13 60727 relates to a method for detecting and identifying a miPEP as defined above, in which the accumulation of said microRNA is determined using a DNA or RNA chip.

The accumulation of said microRNA can be determined using the techniques of molecular biology for assay of molecules of specific nucleic acids.

In another aspect, the subject-matter of application FR 13 60727 also relates to a method for detecting and identifying a microRNA the sequence of the primary transcript of which contains a nucleotide sequence encoding a miPEP, comprising:
  a) a step of detecting an open reading frame of 15 to 303 nucleotides contained in the sequence of the primary transcript of said microRNA. then
  b) a step of comparison between:
    the accumulation of said microRNA in a specified eukaryotic cell expressing said microRNA,
    in the presence of a peptide encoded by a nucleotide sequence that is identical or degenerated relative to that of said open reading frame, said peptide being present in the cell independently of the transcription of the primary transcript of said microRNA, and
    the accumulation of said microRNA in a eukaryotic cell, of the same type as the aforesaid specified eukaryotic cell expressing said microRNA, in the absence of said peptide,
    in which modulation of the accumulation of said microRNA in the presence of said peptide relative to the accumulation of said microRNA in the absence of said peptide indicates the existence of a microRNA the primary transcript of which contains a nucleotide sequence encoding a micropeptide.

In an embodiment, the subject-matter of application FR 13 60727 relates to a method for detecting and identifying a microRNA as defined above, in which the modulation of the accumulation of said microRNA is a decrease or an increase in the accumulation of said microRNA, in particular an increase.

In an embodiment, the subject-matter of application FR 13 60727 relates to a method for detecting and identifying a microRNA as defined above, in which the presence of said peptide in the cell results from:
  the introduction of a nucleic acid encoding said peptide into the cell, or
  the introduction of said peptide into the cell.

In an embodiment, the subject-matter of application FR 13 60727 relates to a method for detecting and identifying a microRNA as defined above, in which said open reading frame in step a) is contained in the 5' or 3' part of said primary transcript of the microRNA. preferably in the 5' part.

In an embodiment, the subject-matter of application FR 13 60727 relates to a method for detecting and identifying a microRNA as defined above, in which said microRNA is present in a wild-type plant cell.

In an embodiment, the subject-matter of application FR 13 60727 relates to a method for detecting and identifying a microRNA as defined above, in which said eukaryotic cell, and said eukaryotic cell of the same type as the aforesaid specified eukaryotic cell, used in step b) are plant cells, preferably cells of Medicago truncatula.

In an embodiment, the subject-matter of application FR 13 60727 relates to a method for detecting and identifying a microRNA as defined above, in which said microRNA is of endogenous origin in said eukaryotic cell and in said eukaryotic cell of the same type as the aforesaid specified eukaryotic cell, used in step b).

In an embodiment, the subject-matter of application FR 13 60727 relates to a method for detecting and identifying a microRNA as defined above in which said microRNA is of exogenous origin in said eukaryotic cell and in said eukaryotic cell of the same type as the aforesaid specified eukaryotic cell, used in step b), said eukaryotic cells containing a vector allowing the expression of said microRNA.

In an embodiment, the subject-matter of application FR 13 60727 relates to a method for detecting and identifying a microRNA as defined above, in which the accumulation of said microRNA is determined using quantitative RT-PCR or Northern blot.

In an embodiment, the subject-matter of application FR 13 60727 relates to a method for detecting and identifying a microRNA as defined above, in which the accumulation of said microRNA is determined using a DNA or RNA chip.

In another aspect, the subject-matter of application FR 13 60727 relates to a miPEP as obtained by applying the method as defined above.

In another aspect, the subject-matter of application FR 13 60727 also relates to a miPEP of 4 to 100 amino acids, preferably of 4 to 40 amino acids, encoded by a nucleotide sequence contained in the primary transcript of a microRNA, said miPEP being capable of modulating the accumulation of said microRNA in a eukaryotic cell.

Moreover, it should be noted that several miORFS can be identified on the primary transcript of a microRNA, indicating that a primary transcript of microRNA can potentially encode several miPEPs.

It should also be noted that the effect of a miPEP is generally specific for a single microRNA, namely that resulting from the primary transcript encoding said miPEP.

In an embodiment, the subject-matter of application FR 13 60727 relates to a miPEP as defined above, said nucleotide sequence being contained in the 5' or 3' part of said primary transcript of a microRNA, preferably in the 5' part.

In an embodiment, the subject-matter of application FR 13 60727 relates to a miPEP as defined above, said nucleotide sequence corresponding to the first open reading frame present on said primary transcript of a microRNA.

In an embodiment, the subject-matter of application FR 13 60727 relates to a miPEP as defined above, said miPEP possessing a basic isoelectric point, preferably above 8.

In another aspect, the subject-matter of application FR 13 60727 relates to a nucleic acid molecule encoding a miPEP as defined above.

In other aspect, the subject-matter of application FR 13 60727 relates to a vector comprising at least one nucleic acid molecule as defined above.

In another aspect, the subject-matter of application FR 13 60727 also relates to the use of at least:
- a miPEP as defined above.
- a nucleic acid encoding said miPEP. or
- a vector containing said nucleic acid.

to modulate the expression of at least one gene in a specified eukaryotic cell, said specified eukaryotic cell being capable of expressing a microRNA the primary transcript of which contains at least one nucleotide sequence encoding said at least one miPEP and the accumulation of which is modulated by said at least one miPEP, the expression of said at least one gene being regulated by said microRNA.

In another aspect, the subject-matter of application FR 13 60727 also relates to the use of at least:
- a miPEP of 4 to 100 amino acids, preferably of 4 to 40 amino acids, encoded by a nucleotide sequence contained in the primary transcript of a microRNA, said miPEP being capable of modulating the accumulation of said microRNA in a eukaryotic cell,
- a nucleic acid encoding said miPEP, or
- a vector containing said nucleic acid, to modulate the expression of at least one gene in a specified eukaryotic cell, said specified eukaryotic cell being capable of expressing a microRNA the primary transcript of which contains at least one nucleotide sequence encoding said at least one miPEP and the accumulation of which is modulated by said at least one miPEP, the expression of said at least one gene being regulated by said microRNA.

The subject-matter of application FR 13 60727 is based on the inventors' surprising observation that it is possible to modulate the expression of one or more target genes of one and the same microRNA by modulating the accumulation of said microRNA using a miPEP.

In an embodiment, the subject-matter of application FR 13 60727 relates to the use as defined above in which said specified eukaryotic cell is a plant cell.

In an embodiment, the subject-matter of application FR 13 60727 relates to the use as defined above in which said microRNA and said gene are of endogenous origin in said specified eukaryotic cell.

In an embodiment, the subject-matter of application FR 13 60727 relates to the use as defined above in which said microRNA and said gene are of exogenous origin in said specified eukaryotic cell, said specified eukaryotic cell containing at least one vector allowing the expression of said microRNA and of said gene.

In application FR 13 60727, the expressions "of endogenous origin" and "of exogenous origin" are used for distinguishing said microRNAs and/or the genes of different species, assuming conservation of the sequences between species.

Thus, the term "of endogenous origin" indicates that the microRNA and or gene can be present naturally in the cell in question. However, other copies of the microRNA and/or of the gene of endogenous origin can be added artificially to the cell in question, for example by cloning.

Conversely, the term "of exogenous origin" indicates that the microRNA and/or gene are never present naturally in the cell in question. It is a microRNA and/or a gene identified in another cellular type or in an organism of another species; this microRNA and/or this gene are therefore necessarily introduced artificially into the cell in question.

In application FR 13 60727, a genetically transformed cell can therefore contain 2 groups of microRNAs and/or of genes that are potentially dose in terms of sequence, one of endogenous origin and the other of exogenous origin.

In another aspect, the subject-matter of application FR 13 60727 relates to a method for modulating the expression of a gene regulated by a microRNA in a eukaryotic cell, comprising carrying out a step of accumulation of a miPEP in said eukaryotic cell, said miPEP having:
- a size of 4 to 100 amino acids, preferably 4 to 20 amino acids, and
- a peptide sequence identical to that encoded by a nucleotide sequence contained in the primary transcript of a microRNA regulating the expression of said gene, and
- being capable of modulating the accumulation of said microRNA, in which the accumulation of said miPEP in said eukaryotic cell induces a modulation of the expression of said gene relative to the expression of said gene without accumulation of said miPEP.

In an embodiment, the subject-matter of application FR 13 60727 relates to a method for modulating the expression of a gene as defined above, in which the accumulation of said miPEP in the cell results from:
- the introduction of a nucleic acid encoding said miPEP into the cell, or
- the introduction of said miPEP into the cell.

In an embodiment, the subject-matter of application FR 13 60727 relates to a method for modulating the expression of a gene as defined above, in which said eukaryotic cell is a plant cell.

In an embodiment, the subject-matter of application FR 13 60727 relates to a method for modulating the expression of a gene as defined above, in which said microRNA and said gene are of endogenous origin in said eukaryotic cell.

In an embodiment, the subject-matter of application FR 13 60727 relates to a method for modulating the expression of a gene as defined above, in which said microRNA and said gene are of exogenous origin in said eukaryotic cell, said eukaryotic cell containing at least one vector allowing the expression of said microRNA and of said gene.

In another aspect, the subject-matter of application FR 13 60727 relates to a modified eukaryotic cell containing a peptide identical to a miPEP as defined above, said peptide being present in said eukaryotic cell independently of the transcription of the primary transcript of the microRNA bearing the nucleotide sequence encoding said miPEP.

In application FR 13 60727, the term "modified eukaryotic cell" means that said eukaryotic cell contains a miPEP introduced artificially into the cell, whether it is as a peptide, or via a vector encoding said miPEP.

In an embodiment, the subject-matter of application FR 13 60727 relates to a modified eukaryotic cell as defined above, in which said microRNA is of endogenous origin.

In another embodiment, the subject-matter of application FR 13 60727 relates to a modified eukaryotic cell as defined above, in which said microRNA is of exogenous origin, said modified eukaryotic cell containing a vector allowing the expression of said microRNA.

In an embodiment, the subject-matter of application FR 13 60727 relates to a modified eukaryotic cell as defined above, said cell being a plant cell.

In another aspect, the subject-matter of application FR 13 60727 relates to a plant comprising at least one modified eukaryotic cell as defined above.

In another aspect, the subject-matter of application FR 13 60727 relates to a composition comprising at least:
- a miPEP as defined above,
- a nucleic acid encoding said miPEP, or
- a vector containing said nucleic acid.

In another aspect, the subject-matter of application FR 13 60727 relates to a pesticide composition comprising at least:
- a miPEP as defined above,
- a nucleic acid encoding said miPEP, or
- a vector containing said nucleic acid.

In another aspect, the subject-matter of application FR 13 60727 relates to a phytopharmaceutical composition comprising at least:
- a miPEP as defined above,
- a nucleic acid encoding said miPEP, or
- a vector containing said nucleic acid.

In another aspect, the subject-matter of application FR 13 60727 relates to an eliciting composition comprising at least:
- a miPEP as defined above,
- a nucleic acid encoding said miPEP, or
- a vector containing said nucleic acid.

By "eliciting composition" is meant a composition capable of giving the plant a better capacity for symbiosis or a better resistance to various stresses, whether they are of a thermal, hydric or chemical nature. To this end, the subject-matter of application FR 13 60727 also relates to compositions acting on the plant's growth (inhibition of growth or conversely increase in growth) and physiology (belter capacity for formation of mycorrhizae and nodulation, better tolerance to various stresses).

In another aspect, the subject-matter of application FR 13 60727 relates to a herbicide composition comprising at least:
- a miPEP as defined above,
- a nucleic acid encoding said miPEP, or
- a vector containing said nucleic acid.

In another aspect, the subject-matter of application FR 13 60727 relates to an insecticide composition comprising at least:
- a miPEP as defined above,
- a nucleic acid encoding said miPEP, or
- a vector containing said nucleic acid.

In another aspect, the subject-matter of application FR 13 60727 relates to the use of a composition as defined above, as a herbicide for eliminating the plants or slowing their growth, preferably as a herbicide specific to a species or to a genus of plants.

In another aspect, the subject-matter of application FR 13 60727 relates to the use of a composition as defined above, as a phytopharmaceutical,
for promoting the growth and/or the development of plants,
in particular for modulating the physiological parameters of a plant, in particular the biomass, leaf surface area, flowering, size of the fruit, production and or selection of plant seeds, in particular for controlling a plant's parthenocarpy or monoecism, or for modifying the physiological parameters of plant seeds, in particular the germination, establishment of the roots, and resistance to water stress,
or for preventing or treating plant diseases.
in particular for promoting resistance to infectious diseases.

In another aspect, the subject-matter of application FR 13 60727 relates to the use of a composition as defined above, for modulating the physiological parameters of a plant, in particular the biomass, leaf surface area, or size of the fruit.

In an embodiment, the subject-matter of application FR 13 60727 relates to the use of a composition as defined above, for thinning orchards in order to increase the size of the fruit.

In an embodiment, the subject-matter of application FR 13 60727 relates to the use of a composition as defined above, for the production and or selection of plant seeds, said composition being used for controlling a plant's parthenocarpy or monoecism.

In an embodiment, the subject-matter of application FR 13 60727 relates to the use of a composition as defined above, said composition being administered to said plant via the leaves or via the roots.

In an embodiment, the subject-matter of application FR 13 60727 relates to the use of a composition as defined above, for the production and or selection of plant seeds.

In an embodiment, the subject-matter of application FR 13 60727 relates to the use of a composition as defined above, in which said composition is used for modifying the physiological parameters of said plant seeds, in particular establishment of the roots, germination and resistance to water stress.

In an embodiment, the subject-matter of application FR 13 60727 relates to the use of a composition as defined above, in which said composition is applied by coating or forming a film on said plant seeds.

In another aspect, the subject-matter of application FR 13 60727 relates to the use of a composition as defined above, as a pesticide for eliminating organisms that are harmful to the plants or that can be classified as such, in particular as insecticide, arachnicide, molluscicide or rodenticide.

In an embodiment, the subject-matter of application FR 13 60727 relates to the use of a composition as defined above, as insecticide.

In an embodiment, the subject-matter of application FR 13 60727 relates to the use of a composition as defined above, for eliminating insect pests.

In an embodiment, the subject-matter of application FR 13 60727 relates to the use of a composition as defined above, for eliminating animal species that are classified as harmful or that can be classified as such, in particular the Muridae, in particular the rat.

In another aspect, the subject-matter of application FR 13 60727 relates to the use of a composition as defined above, in which said composition is applied onto a plant to protect it against insect pests.

The following figures and examples will better illustrate the invention, without limiting its scope.

CAPTIONS TO THE FIGURES

FIG. 1. Effects of a treatment with miPEP164a on the expression of miR164a in *A. thaliana*.

The photographs show the results of a Northern blot analysis of the accumulation of miR164a in roots treated with water (control, photograph on the left) or with 0.1 µM of a synthetic peptide, having a sequence identical to that of miPEP164a, solubilized in water (0.1 µM miPEP164a). The RNA U6 is used as a loading control, allowing the quantity of miR164a to be quantified.

This experiment was repeated 4 times independently, leading to similar results.

Treatment of shoots of *A. thaliana* with 0.1 µM of miPEP164a leads to an increase in the accumulation of miR164a.

Figure 2:
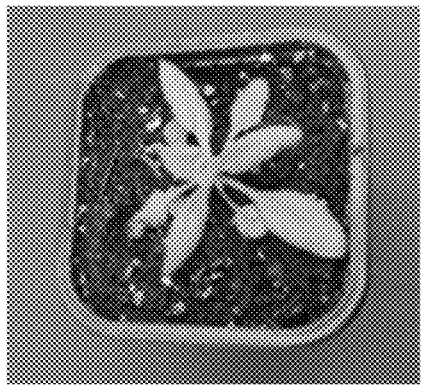
Figure 2:
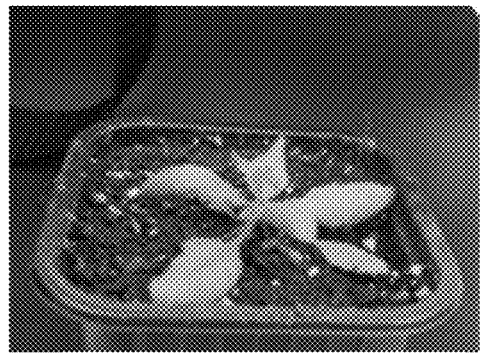
Figure 2:
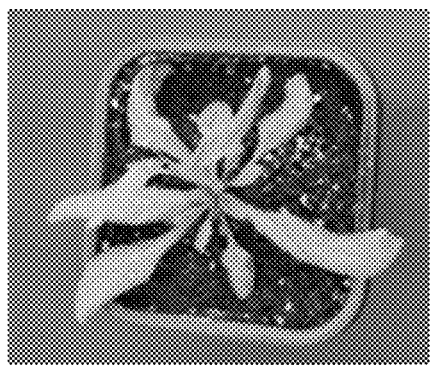
Figure 2:

FIG. 2. Effects of treatment with miPEP164a on the growth of *Arabidopsis thaliana*.

The photographs show two plants (top views and side views) after 3 weeks of growth: a control plant watered and sprayed with water (A) and a plant watered and sprayed with a composition of 0.1 µM of synthetic peptide the sequence of which is identical to miPEP164a (B). Watering plants of *Arabidopsis thaliana* with miPEP164a increases the plant's growth significantly.

Figure 3:

FIG. 3. Effects of treatment with miPEP164a on the date of flowering in *Arabidopsis thaliana*

The photographs show two plants after 39 days of growth: a control plant watered and sprayed with water (photograph on the left) and a plant watered and sprayed with a composition of 1 µM of synthetic peptide the sequence of which is identical to miPEP164a (photograph on the right). Watering plants of *Arabidopsis thaliana* with miPEP164a increases the plant's growth and number of flowers significantly.

Figure 4:
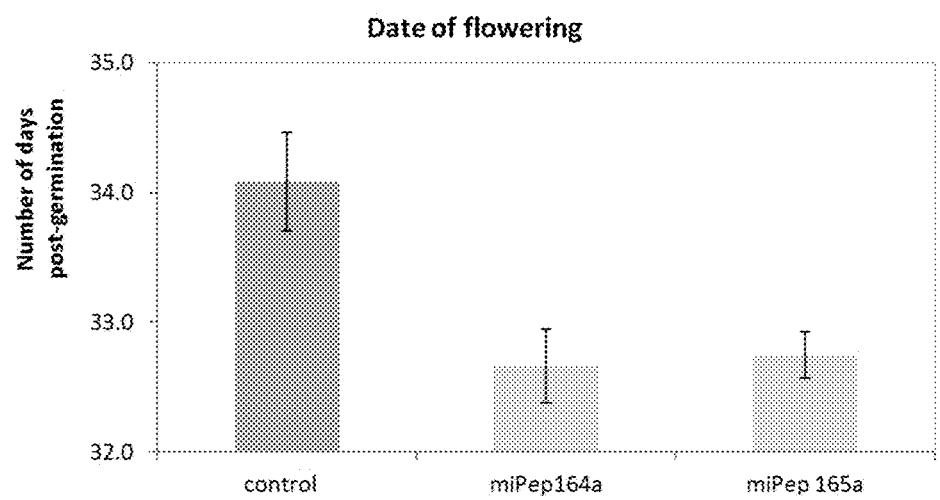

FIG. 4. Effects of treatment with miPEP164a on the date of flowering in *Arabidopsis thaliana*

The y-axis shows the number of days after germination to the date of flowering in a plant treated with water (left bar) or with a composition containing 1 µM of miPEP164a (middle bar) and 1 µM of miPEP165a (right bar).

The error bar corresponds to the standard error of the mean (number of individuals=12 control plants, 12 treated plants).

This experiment was repeated independently, leading to similar results.

Figure 5:
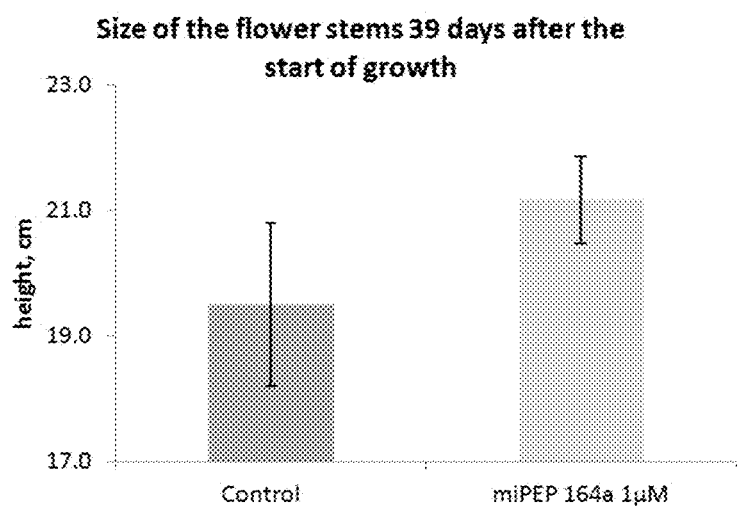

FIG. 5. Effects of treatment with miPEP164a on the size of the floral stalks in *Arabidopsis thaliana*

The y-axis shows the height of the floral stalk in a plant treated with water (left bar) or with a composition containing 0.1 µM of miPEP164a (right bar).

The error bar corresponds to the standard error of the mean (number of individuals=12 control plants, 12 treated plants).

Figure 6:
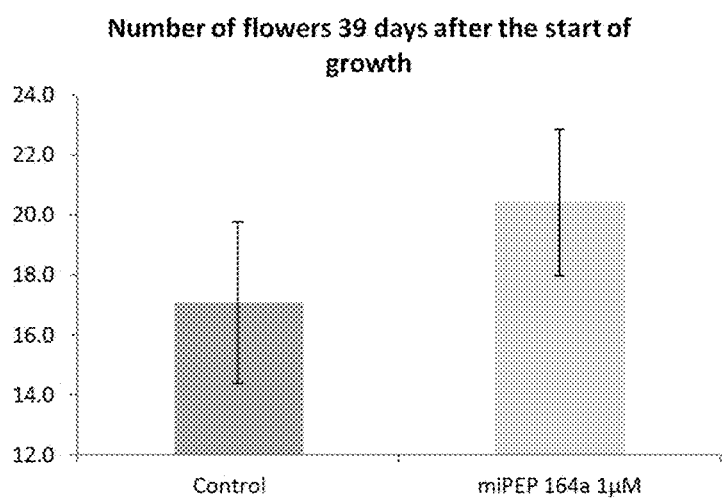

FIG. 6. Effects of treatment with miPEP164a on the number of flowers in *Arabidopsis thaliana*

The y-axis shows the number of flowers after 39 days of growth in a plant treated with water (left bar) or with a composition containing 0.1 µM of miPEP164a (right bar).

The error bar corresponds to the standard error of the mean (number of individuals=12 control plants, 12 treated plants).

Figure 7:
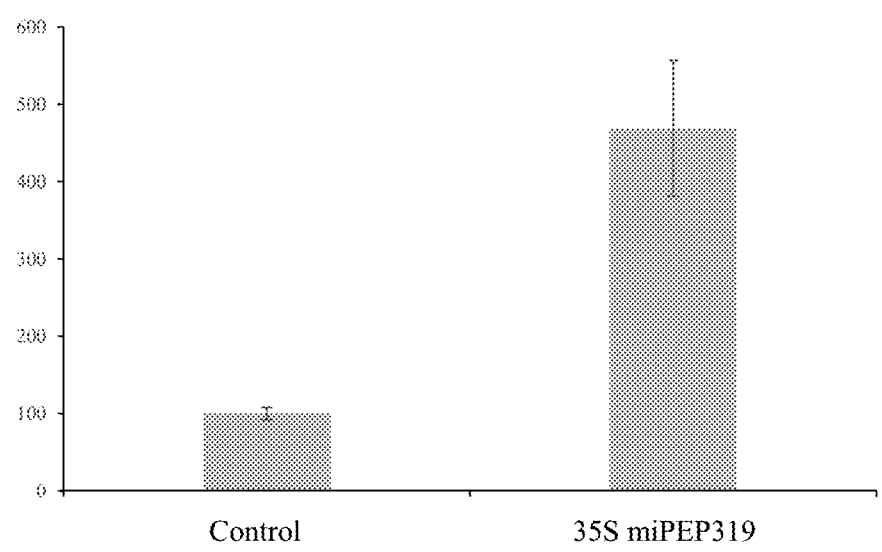

FIG. 7. Effects of the overexpression of AtmiPEP319a on the expression of AtmiR319a in *A. thaliana*.

The y-axis shows the relative expression of AtmiR319a in a control plant (left column) or in a plant in which AtmiPEP319a is overexpressed (right column). The error bar corresponds to the standard error of the mean (number of individuals=10). The overexpression of AtmiPEP319a induces an increase in the accumulation of Atmir319a.

Figure 8:
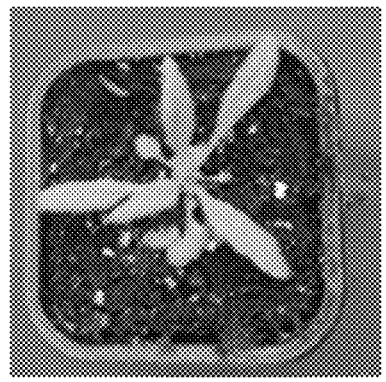
Figure 8:
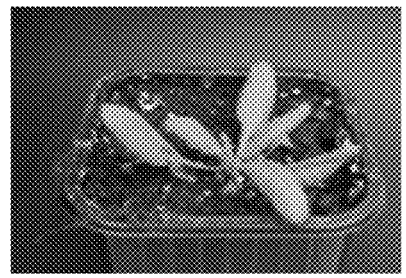
Figure 8:
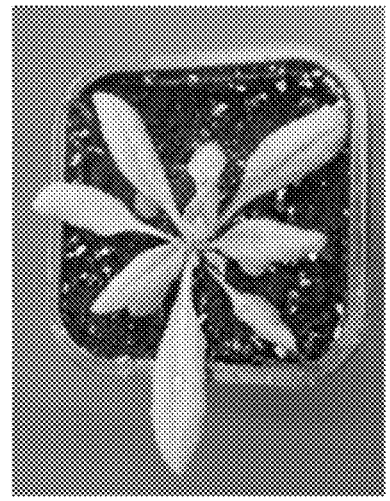
Figure 8:
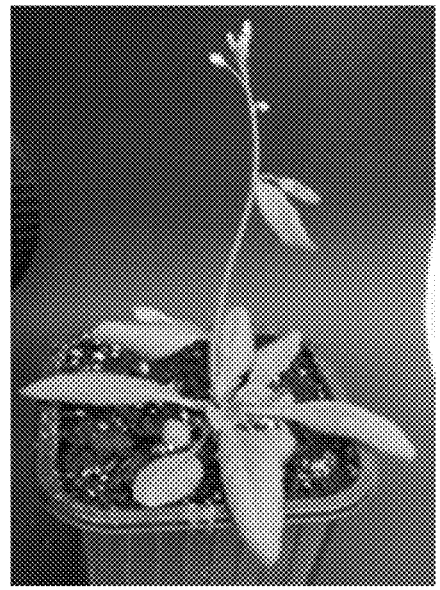

FIG. 8. Effects of treatment with miPEP319a on the growth of *Arabidopsis thaliana*.

The photographs show two plants (top views and side views) after 3 weeks of growth: a control plant watered and sprayed with water (A) and a plant watered and sprayed with a composition of 0.1 µM of synthetic peptide the sequence of which is identical to miPEP319a (B). Watering plants of *Arabidopsis thaliana* with miPEP319a increases the plant's growth significantly.

EXAMPLES

Example A1—Identification and Characterization of miPEP164a

In order to identify miPEPs encoded by pri-miRNAs of plants, ORFS were investigated in RACE-PCR data (Xie et al., *Plant Physiol*, 138:2145-54, 2005), in which the sequences of the 5' end of the pri-miRNA of 50 miRNAs of *A. thaliana* are available.

ORFs capable of encoding peptides of from 4 to 59 amino acids were identified in each of the pri-miRNAs, and in particular an miORF, identified on the pri-miRNA of miR164a, capable of encoding a peptide miPEP164a.

To test whether this peptide really is a miPEP, the latter was synthesized and was used for investigating an increase in the accumulation of miR164a in roots of *A. thaliana* treated with the synthetic peptide. Northern blot analyses show that treatment of the plant with the peptide miPEP164a leads to an increase in the accumulation of miR164a (FIG. 1).

Moreover, growth experiments were also carried out on *A. thaliana* plants and they show that watering *A. thaliana* plants with miPEP164a increases the plants' growth significantly (FIG. 2).

Example A2—Material and Methods

Plants

The *A. thaliana* Col-0 plants are cultivated on MS basic medium supplemented with 10 g/l of sucrose.

Peptides

The peptides were synthesized by Smartox and were solubilized in water.

Northern Blot

Northern blot analysis was carried out according to the protocol described in Lauressergues et al. *Plant J,* 72(3): 512-22, 2012.

The biological samples were homogenized in a buffer containing 0.1 M of NaCl, 2% SDS, 50 mM of Tris-HCl (pH 9), 10 mM of EDTA (pH 8) and 20 mM of mercaptoethanol, and the RNA was extracted twice with a phenol/chloroform mixture and precipitated with ethanol.

The RNA was loaded on PAGE 15% gel and transferred onto a nylon membrane (HybondNX, Amersham). The RNA was hybridized with an oligonucleotide probe, with radioactive labelling at its end, for detecting the RNA U6 or for miR164a.

The hybridizations were carried out at 55° C. The hybridization signals were quantified using a phosphorimager (Fuji) and normalized with the signal of the probe specific to the RNA U6.

*A. thaliana* Growth Test

*Arabidopsis thaliana* seeds were germinated on GiFi, and then were transferred onto compost and were grown for 3 weeks.

Watering was carried out every 2-3 days with water for the control plants and with water containing 0.1 µM or 1 µM of synthetic peptide (the sequence of which is identical to miPEP164a or to miPEP165a) for the test plants.

Example B1—Identification and Characterization of miPEP319a

In order to identify miPEPs encoded by pri-miRNAs of plants, ORFS were investigated in RACE-PCR data (Xie et al., *Plant Physiol*, 138:2145-54, 2005), in which the sequences of the 5' end of the pri-miRNA of 50 miRNAs of *A. thaliana* are available. ORFs capable of encoding peptides of 4 to 59 amino acids were identified in each of the pri-miRNAs, and in particular an miORF, identified on the pri-miRNA of miR319a, capable of encoding a peptide miPEP319a.

To test whether this peptide is really a miPEP, the latter was synthesized and was used for investigating an increase in the accumulation of miR319a in roots of *A. thaliana* treated with the synthetic peptide. Analyses by qPCR show that the overexpression of AtmiPEP319a induces an increase in the accumulation of Atmir319a (FIG. 7).

In addition, growth experiments were also carried out on *A. thaliana* plants and show that watering and spraying *A. thaliana* plants with miPEP319a increases the plant's growth significantly (FIG. 8).

Example B2-Material and Methods

Plants

The *A. thaliana* Col-O plants are cultivated on MS basic medium supplemented with 10 g/l of sucrose.

Peptides

The peptides were synthesized by Smartox and were solubilized in a solution of 40% water/50% acetonitrile/10% acetic acid (v/v/v).

Reverse Transcription of the microRNAs

The RNA was extracted using the reagent Tri-Reagent (MRC) according to the manufacturer's instructions, apart from precipitation of the RNA, which was carried out with 3 volumes of ethanol. Reverse transcription of the RNA was carried out using the stem-loop specific primer RTprimer in combination with hexamers in order to carry out reverse transcription of RNA of high molecular weight. Briefly, 1 µg of RNA was added to the stem-loop specific primer (0.2 µM), hexamer (500 ng), buffer RT (1×), the enzyme SuperScript Reverse transcriptase (SSIII) (one unit), dNTPs (0.2 mM each), DTT (0.8 mM) in a final reaction mixture of 25 µl. In order to carry out the reverse transcription, a pulsed reverse transcription reaction was carried out (40 repetitions of the following cycle: 16° C. for 2 minutes, 42° C. for one minute and 50° C. for one second, followed by final inactivation of the reverse transcription at 85° C. for 5 minutes).

Analyses by Quantitative RT-PCR (qRT-PCR)

The total RNA of the roots of *M. truncatula* or of the leaves of tobacco was extracted using the extraction kit RNeasy Plant Mini Kit (Qiagen). Reverse transcription was carried out using the reverse transcriptase SuperScript II (Invitrogen) starting from 500 ng of total RNA. Three repetitions (n=3) were carried out, each with two technical repetitions. Each experiment was repeated two or three times. qPCR amplifications were carried out using a thermocycler LightCycler 480 System (Roche Diagnostics) by the method described in Lauressergues et al. (*Plant J.*, 72(3):512-22, 2012).

Plasmid Constructs

The DNA fragments of interest were amplified with Pfu polymerase (Promega). The DNA fragments were cloned for overexpression under the control of the strong constitutive promoter 35S by the method described in Combier et al. (*Genes & Dev*, 22:1549-1559, 2008). miORF319a was cloned in pBIN19 by the method described in Combier et al. (*Genes & Dev*, 22:1549-1559, 2008).

Statistical Analyses

The mean values of the relative expression of the genes or of the production of lateral roots were analysed using the Student test or the Kruskal-Wallis test. The error bars represent the standard error of the mean (SEM). The asterisks indicate a significant difference (p<0.05).

*A. thaliana* Growth Test

*Arabidopsis thaliana* seeds were germinated on GiFi, and then were transferred onto compost and were grown for 3 weeks.

Watering was carried out every 2-3 days and spraying was carried out every day, with water for the control plants and with water containing 0.1 µM of synthetic peptide (the sequence of which is identical to miPEP319a) for the test plants.

The invention claimed is:

1. A method for promoting the growth of a plant comprising administering to said plant a composition comprising a micropeptide (miPEP) in a concentration from $10^{-9}$ M to $10^{-4}$ M,
said miPEP being selected from the group consisting of: miPEP164a, miPEP165a and miPEP319a,
wherein said miPEP164a has an amino acid sequence consisting of SEQ ID NO: 2, said miPEP165a has an amino acid sequence consisting of SEQ ID NO: 6 and said miPEP319a has an amino acid sequence consisting of SEQ ID NO: 10.

2. The method according to claim 1, in which said plant is a cruciferous plant.

3. A composition comprising:
miPEP164a as an active ingredient, said miPEP164a being at a concentration of from $10^{-9}$ M to $10^{-4}$ M,
miPEP165a as an active ingredient, said functional miPEP165a being at a concentration of from $10^{-9}$ M to $10^{-1}$ M,
miPEP319a as an active ingredient, said functional miPEP319a being at a concentration of from $10^{-9}$ M to $10^{-4}$ M,
said composition further comprising an excipient, a diluent or a solvent,
wherein said excipient, diluent or a solvent comprises water, acetonitrile and acetic acid and
wherein said miPEP164a has an amino acid sequence consisting of SEQ ID NO: 2, said miPEP165a has an amino acid sequence consisting of SEQ ID NO: 6 and said miPEP319a has an amino acid sequence consisting of SEQ ID NO: 10.

4. A composition comprising, in combination, a quantity of seeds from a plant and a quantity of a miPEP, the sequence of which comprises or consists of a sequence identical to that of a miPEP naturally present in said plant, said miPEP having a sequence consisting of SEQ ID NO:2, SEQ ID NO:6 or SEQ ID NO:10, said miPEP being at a concentration of from $10^{-9}$ M to $10^{-4}$ M in the composition, wherein said miPEP is coated onto said quantity of seeds.

5. The method according to claim 1, wherein said miPEP is administered to the plant by watering, by spraying or by adding a fertilizer, a compost, a culture substrate or a support in contact with the plant.

6. The composition according to claim 3, wherein said composition is formulated so as to form a coating.

* * * * *

UNITED STATES PATENT AND TRADEMARK OFFICE
CERTIFICATE OF CORRECTION

PATENT NO. : 10,563,214 B2  
APPLICATION NO. : 15/314519  
DATED : February 18, 2020  
INVENTOR(S) : Jean-Philippe Combier et al.

It is certified that error appears in the above-identified patent and that said Letters Patent is hereby corrected as shown below:

In the Claims

Column 39, Claim 3, Line 33 correct "$10^{-1}$ M," to "$10^{-4}$ M,"

Signed and Sealed this  
Second Day of June, 2020

Andrei Iancu  
*Director of the United States Patent and Trademark Office*